US008034008B2

(12) United States Patent
Hovorka

(10) Patent No.: US 8,034,008 B2
(45) Date of Patent: Oct. 11, 2011

(54) ACCESS PORT FOR FLEXIBLE WOUND TREATMENT DEVICES

(75) Inventor: George Hovorka, East Boston, MA (US)

(73) Assignee: AOTI, Inc., Tamarac, FL (US)

( * ) Notice: Subject to any disclaimer, the term of this patent is extended or adjusted under 35 U.S.C. 154(b) by 406 days.

(21) Appl. No.: 12/291,338

(22) Filed: Nov. 7, 2008

(65) Prior Publication Data

US 2009/0143720 A1 Jun. 4, 2009

Related U.S. Application Data

(60) Provisional application No. 61/002,268, filed on Nov. 7, 2007, provisional application No. 61/002,269, filed on Nov. 7, 2007, provisional application No. 61/127,809, filed on May 15, 2008, provisional application No. 61/192,287, filed on Sep. 17, 2008.

(51) Int. Cl.
*A61F 5/00* (2006.01)

(52) U.S. Cl. .......................................... 602/13; 600/21

(58) Field of Classification Search .................... 602/13; 600/21-22; 128/202.12; 5/706
See application file for complete search history.

(56) References Cited

U.S. PATENT DOCUMENTS

| | | | | |
|---|---|---|---|---|
| 871,760 | A | | 11/1907 | Long et al. |
| 1,117,168 | A | | 11/1914 | Crowley |
| 2,134,646 | A | | 10/1938 | Sauzedde |
| 3,368,556 | A | | 2/1968 | Jensen et al. |
| 3,478,738 | A | | 11/1969 | Altman et al. |
| 3,602,221 | A | | 8/1971 | Bleiken |
| 3,604,421 | A | | 9/1971 | Pizzella |
| 3,669,096 | A | | 6/1972 | Hurwitz |
| 3,701,349 | A | | 10/1972 | Larson |
| 3,712,298 | A | | 1/1973 | Snowdon et al. |
| 3,744,491 | A | * | 7/1973 | Fischer ............................ 604/23 |
| 3,785,374 | A | | 1/1974 | Lipson |
| 3,920,006 | A | | 11/1975 | Lapidus |
| 3,955,565 | A | | 5/1976 | Johnson, Jr. |
| 4,003,371 | A | * | 1/1977 | Fischer ............................ 604/23 |
| 4,211,223 | A | | 7/1980 | LoPiano |

(Continued)

FOREIGN PATENT DOCUMENTS

WO 2006091243 8/2006

OTHER PUBLICATIONS

International Search Report, PCT/US08/12535, dated Dec. 25, 2008.

(Continued)

*Primary Examiner* — Michael A. Brown
(74) *Attorney, Agent, or Firm* — Lerner, David, Littenberg, Krumholz & Mentlik, LLP

(57) ABSTRACT

A limb wound treatment device is described having a first end, a second end and an interior therebetween for accommodating a treatment gas. The device can include a flexible housing that can be inflated. The first end can include an inflatable cuff seal for hermetically sealing against the limb being treated. The second end can include a closed end or an access port that is releasably sealed with a clamping mechanism. Further, the device can include a controller that can inflate that housing, inflate the cuff seal and provide treatment gas to the interior, in response to pressures within the cuff seal and the housing. Further, the device can accommodate different types of wound treatments, such as hyperbaric therapy, compression therapy or negative pressure therapy.

17 Claims, 29 Drawing Sheets

U.S. PATENT DOCUMENTS

| | | | | |
|---|---|---|---|---|
| 4,227,524 | A | | 10/1980 | Galerne |
| 4,236,513 | A | | 12/1980 | LoPiano |
| 4,280,489 | A | | 7/1981 | Johnson, Jr. |
| 4,328,799 | A | | 5/1982 | LoPiano |
| 4,331,133 | A | | 5/1982 | Arkans |
| 4,346,699 | A | | 8/1982 | Little et al. |
| 4,353,359 | A | | 10/1982 | Milbauer |
| 4,363,317 | A | | 12/1982 | Broucek |
| 4,378,009 | A | | 3/1983 | Rowley et al. |
| 4,460,370 | A | | 7/1984 | Allison et al. |
| 4,628,945 | A | | 12/1986 | Johnson, Jr. |
| 4,633,859 | A | | 1/1987 | Reneau |
| 4,635,635 | A | | 1/1987 | Robinette-Lehman |
| 4,667,672 | A | | 5/1987 | Romanowski |
| 4,801,291 | A | | 1/1989 | Loori |
| 5,029,579 | A | | 7/1991 | Trammell |
| 5,060,644 | A | | 10/1991 | Loori |
| 5,125,400 | A | | 6/1992 | Johnson, Jr. |
| 5,154,697 | A | | 10/1992 | Loori |
| 5,211,642 | A | | 5/1993 | Clendenning |
| 5,234,459 | A | | 8/1993 | Lee |
| 5,264,218 | A | | 11/1993 | Rogozinski |
| 5,312,385 | A | | 5/1994 | Greco |
| 5,376,067 | A | | 12/1994 | Daneshvar |
| 5,437,602 | A | | 8/1995 | Polyakov et al. |
| 5,458,562 | A | | 10/1995 | Cooper |
| 5,478,310 | A | | 12/1995 | Dyson-Cantwell et al. |
| 5,578,055 | A | | 11/1996 | McEwen |
| 5,605,534 | A | | 2/1997 | Hutchison |
| 5,620,001 | A | | 4/1997 | Byrd et al. |
| 5,660,182 | A | | 8/1997 | Kuroshaki et al. |
| 5,669,390 | A | | 9/1997 | McCormick et al. |
| 5,678,543 | A | | 10/1997 | Bower |
| 5,688,236 | A | | 11/1997 | Gragg |
| 5,738,093 | A | | 4/1998 | Santi |
| 5,810,795 | A | | 9/1998 | Westwood |
| 5,848,998 | A | * | 12/1998 | Marasco, Jr. .................. 604/290 |
| 5,865,722 | A | * | 2/1999 | Heng .............................. 600/21 |
| 6,235,365 | B1 | | 5/2001 | Schaughency et al. |
| 6,321,746 | B1 | | 11/2001 | Schneider et al. |
| 6,622,326 | B2 | | 9/2003 | Richardson |
| 6,702,794 | B2 | | 3/2004 | Blum et al. |
| 6,814,720 | B2 | | 11/2004 | Olsen et al. |
| 6,881,929 | B2 | | 4/2005 | Hovorka |
| 2003/0036771 | A1 | | 2/2003 | McEwen et al. |
| 2005/0043672 | A1 | | 2/2005 | Piuk et al. |
| 2005/0161039 | A1 | | 7/2005 | Gurnee et al. |
| 2006/0185670 | A1 | | 8/2006 | Loori et al. |
| 2008/0140029 | A1 | | 6/2008 | Smith et al. |
| 2009/0126727 | A1 | | 5/2009 | Loori et al. |

OTHER PUBLICATIONS

U.S. Appl. No. 61/002,269; filed Nov. 7, 2007, entitled "Pressure Compensating Seal With Positive Feedback".

U.S. Appl. No.11/064,581; Feb. 24, 2005, entitled "Hyperbaric Oxygen Device and Delivery methods".

U.S. Appl. No. 12/156,465; filed May 30, 2008, entitled "Controller for an Extremity Hyperbaric Chamber".

U.S. Appl. No. 12/156,466, filed May 30, 2008, entitled "Controller for an Extremity Hyperbaric Chamber".

U.S. Appl. No. 12/291,317.

U.S. Appl. No. 12/291,348.

U.S. Appl. No. 12/291,328.

U.S. Appl. No. 12/291,342.

U.S. Appl. No. 12/291,347.

International Search Report, PCT/US08/06883.

The Topical Hyperbaric Oxygen Extremity Chamber.

The Disposable Sacral Topical Hyperbaric Oxygen System.

Dutton, et al. "Topical Hyperbaric Oxygen Therapy: A Case Study" Macassa Lodge, Hamilton, Ontario.

Heng, et al. "Angiogenesis in Necrotic Ulcers Treated with Hyperbaric Oxygen" OstomyWound Management, Sep. 2000, vol. 46, Issue 9, pp. 18-32.

Edsberg, et al. "Use of Topical Hperbaric Oxygen for Treatment of Chronic Wounds in Long-Termn Health Care Facilities" Natural & Health Sciences Research Center, Daemen College, Amherst, NY.

Edsberg, et al. "Reducing Epibole Using Topical Hyerpbaric Oxygen and Electrical Stimulation" OstomyWound Management Apr. 2002, vol. 48, Issue 4, pp. 26-29.

Diamond, et al. "The Effect of Hyperbaric Oxygen on Lower Extremity Ulcerations" Journal of the American Podiatry Association, vol. 72, No. 4, Apr. 1982, pp. 180-185.

Lehman, et al. "Human Bite Infections of the Hand: Adjunct Treatment with Hyperbaric Oxygen" Orthopedic Complications, Infections in Surgery, Jun. 1985, pp. 460-465.

Fischer "Topical Hyperbaric Oxygen Treatment of Pressure Sores and Skin Ulcers" reprinted from The Lancet, Aug. 23, 1969, pp. 405-409.

Upson "Topical Hyperbaric Oxygenation in the Treatment of Recalcitrant Open Wounds—A clinical report" Physical Therapy, vol. 66, No. 9, Sep. 1986, pp. 1408-1411.

Fischer "Treatment of Ulcers on the Legs with Hyperbaric Oxygen" reprinted from the Journal of Dermatologic Surgery, Inc. vol. 1, No. 3, Oct. 1975, J of Derm Surg 1:3, Oct. 1975, pp. 55-58.

Heng "Topical Hyperbaric Therapy for Problem Skin Wounds" J Dermatol Surg Oncol. 1993 Aug; 19(8):784-93, Department of Medicine, UCLA San Fernando Valley Internal Medicine Program, Veterans Administration Medical Center, Sepulveda, PMID: 8349920 [PubMed—indexed for Medline].

Kalliainen, et al. "Topical oxygen as an adjunct to wound healing: A clinical case series" ISP Pathophysiology 9 (2003) 81-87, 2002 Elsevier Science Ireland Ltd.

Kaufman, et al., "Topical oxygen and burn wound healing: A review" Shriners Burns Institute, Cincinnati Unit, Ohio.

Olejniczak, et al. "Topical Oxygen Promotes Healing of Leg Ulcers" Dec. 1976, Medical Times, vol. 104, No. 12, pp. 115-120.

Fries, et al., "Dermal excisional wound healing in pigs following treatment with topically applied pure oxygen" Mutat. Res. 2005 Nov. 11; 579(1-2): 172-81 Epub Aug 18, 2005 Laboratory of Molecular Medicine, Dorothy M. Davis Heart and Lung Research Institute and Comprehensive Wound Center, Department of Surgery, The Ohio State University Medical Center, Columbus, OH, PMID: 16105672 [PubMed—in process].

Stryker—Taoti Advanced Oxygen Therapy, Inc. Wound Care Solution Excellence, Strategic Discussions Kalamazoo, Michigan, Mar. 21, 2007 powerpoint presentation, 96 pages.

Venous Ulcers Appendix I, Evidence Table per FDA Draft Guidance Document, 8 pages.

Clinical Device Group and the Food and Drug and Law Institute are happy to present: "Getting CMS Reimbursement for Medical Technology Product" 2006, Clinical Device Group, Inc. Powerpoint presentation, 78 pages.

Medical Coverage Advisory Committee, Usual Care of Chronic Wounds, Powerpoint presentation, 144 pages.

CDC Diabetes, Department of Health and Human Services, Centers for Disease Control and Prevention, "National Diabetes Fact Sheet", United States, 2003, General Information, 3 pages.

Pompeo "The Role of "Wound Burden" in Determining the Costs associated with Wound Care" OstonomyWound Management, Mar. 2001, vol. 47, Issue 3, pp. 65-71.

Frykberg, et al. "Diabetic Foot Disorders: A Clinical Practice Guideline" 2006 revision, The Journal of Foot and Ankle Surgery, vol. 45, No. 5, Sep./Oct. 2006, S1-S66.

American Diabetes Association, "Economic Costs of Diabetes in the U.S. In 2002" Diabetes Care, vol. 26, No. 3, Mar. 2003, pp. 917-932.

Snyder, et al. OstomyWound—Osteomyelitis in the Diabetic Patient: Overview, Diagnosis, Microbiology, "Osteomyelitis in the Diabetic Patient: Diagnosis and Treatment Part 1: Overview, Diagnosis, and Microbiology" (Abstract).

Branom, et al., "Constant Force Technology' versus Low-Air-Loss Therapy in the Treatment of Pressure Ulcers", OstomyWound—Utilizing a Systems Approach to Implement Pressure Ulcer Prediction and Prevention, Sep. 2001, vol. 47, Issue 9, pp. 38-39.

Landau, et al. "Topical hyperbaric oxygen and low energy laser therapy for chronic diabetic foot ulcers resistant to conventional treatment" Yale J. Biol. Med. 2001 Mar-Apr; 74(2):95-100, The Hebrew University, Hadassah School of Medicine, Jerusalem, Israel. PMID: 11393266 [PubMed—indexed for Medline].

Sen, et al. "Oxygen, oxidants, and antioxidants in would healing: An emerging paradigm" Laboratory of Molecular Medicine, Dorothy M. Davis Heart and Lung Research Institute, Department of Surgery (CMIS), The Ohio State University Medical Center, Columbus, OH, Ann N. Y. Acad. Sci. May 2002; 957:239-49, PMID: 12074976 [PubMed—indexed for Medline].

Gordillo, et al. "Revisiting the essential role of oxygen in wound healing" Department of Surgery, Laboratory of Molecular Medicine, 512 Davis Heart and Lung Research Institute, The Ohio State University, 473 West 12th Ave., Columbus, OH, Am. J. Surg. Sep. 2003;186(3):259-63, PMID: 12946829 [PubMed—indexed for Medline].

Ignacio, et al. "Topical Oxygen Therapy Treatment of Extensive Leg and Foot Ulcers" Journal of the American Podiatric Medical Association, vol. 75, No. 4, Apr. 1985, pp. 196-199.

Cianci "Advances in the treatment of the diabetic foot: Is there a role for adjunctive hyperbaric oxygen therapy?" Wound Repair Regen, Jan.-Feb. 2004; 129(1):2-10, Department of Hyperbaric Medicine, Doctors Medical Center, San Pablo, California, PMID: 14974958 [PubMed—indexed for Medline].

Hopf, et al. "Hyperoxia and angiogenesis" Blackwell Synergy: Wound Repair Regen, vol. 13, Issue 6, pp. 558-564: Hyperoxia and angiogenesis (Abstract); Wound Repair and Regeneration vol. 13 Issue 6 p. 558—Nov. 2005; http://www.blackwell-synergy.com/doi/abs/10.1111/j.1524-475X.2005.00078.x(1of 3)Dec. 19, 2006.

Kaufman, et al. "The Microclimate Chamber: The Effect of Continuous Topical Administration of 96% Oxygen and 75% Relative Humidity on the Healing Rate of Experimental Deep Burns" The Journal of Trauma, vol. 23, No. 9, pp. 806-815.

Heng, et al. "Endothelial cell toxicity in leg ulcers treated with topical hyperbaric oxygen" Am. J. Dermatopathol Oct. 1986 8(5):403-10; MID: 3777378 [PubMed—indexed for MEDLINE].

Heng, et al. "Enhanced Healing and Cost-Effectiveness of Low—Pressure Oxygen Therapy in Healing Necrotic Wounds: A feasibility study of technology transfer" Ostomy/Wound Management 2000; 46(3):52-62; From the Division of Dermatology, Department of Medicine, Department of Veterans Affairs, VAGLAHS (Sepulveda), UCLA San Fernando Valley Program, pp. 52-60.

Harkless, et al. "Seven keys to Treating Chronic Wounds" Diabetes Watch, Podiatry Today, Dec. 2000, pp. 17-19.

Diabetes Care, published by the American Diabetes Association "Study Finds Diabetes Will Double in World by 2030: Predicts Rapid U.S. increase That Greatly Exceeds Prior CDC Projections" lead author Dr. Sarah Wild, Public Health Sciences, University of Edinburgh, 2 pages.

Rossi, Hudson Podiatry Center, Letter.

International Search Report, PCT/US2008/12669, dated Dec. 27, 20008.

International Search Report, PCT/US2008/12625, dated Dec. 22, 2008.

* cited by examiner

ACCESS PORT FOR FLEXIBLE WOUND TREATMENT DEVICES

CROSS-REFERENCE TO RELATED APPLICATIONS

This application claims the benefit of the filing date of U.S. Provisional Patent Application No. 61/127,809, filed May 15, 2008, entitled "Access Port For Single Use Wound Treatment Devices," the disclosure of which is hereby incorporated herein by reference.

This application claims the benefit of the filing date of U.S. Provisional Patent Application No. 61/192,287, filed on Sep. 17, 2008, entitled, "Triple Modality Wound Treatment Device," the disclosure of which is incorporated herein be reference.

This application claims the benefit of the filing date of U.S. Provisional Patent Application No. 61/002,269 filed Nov. 7, 2007, entitled, "Compensating Seal with Positive Feedback," the disclosure of which is hereby incorporated herein by reference.

This application claims the benefit of the filing date of U.S. Provisional Patent Application No. 61/002,268 filed Nov. 7, 2007, entitled, "Hyperbaric Device," the disclosure of which is hereby incorporated herein by reference.

BACKGROUND OF THE INVENTION

Wound treatment devices create sealed environments for the application of therapeutic gases to hasten healing of lesions or wounds on a patient's body. As described in U.S. Pat. No. 5,060,644, entitled "Hyperbaric Chamber Apparatus," the disclosure of which is incorporated herein by reference, the introduction of pressurized gas, such as oxygen, into such an encapsulated environment promotes healing of various types of lesions and wounds.

When wound treatment devices were first introduced for healing of wounds, they enclosed the entire body. As time progressed, these devices became more sophisticated, and covered and treated a portion of a patient's body, such as described in U.S. Pat. No. 5,154,697 entitled, "Collapsible Topical Hyperbaric Apparatus" and U.S. Pat. No. 4,801,291, entitled, "Portable Topical Hyperbaric Apparatus," which are incorporated by reference herein. These devices could be used to treat a patient's wound or lesion without the need to surround the entire body.

Given that these devices are used to treat open wounds, there is the possibility of transferring infection from one patient to another. Thus, time and effort are expended to clean and sterilize those devices that were intended for reuse. Accordingly, there is a need for a wound treatment device that eliminates the likelihood of infection and, further, may be less expensive to manufacture and use than conventional wound treatment devices. Further, there is a need for an improved sealing mechanism for hyperbaric treatment devices to prevent leakage of valuable treatment gas. In addition, there is also a need to provide easy access to the limb being treated. Lastly, a wound treatment device is desired that can accommodate a variety of wound treatments, such as hyperbaric treatment, compression therapy and negative pressure treatment.

SUMMARY OF THE INVENTION

Embodiment A

In an embodiment of the present invention, a wound treatment device can include a flexible housing having an interior for accommodating treatment gas. The housing can have a first end for accommodating a patient's limb and a second end remote from the first end having an access port, and a clamping mechanism for sealing and unsealing the access port.

In another embodiment of the present invention, a wound treatment device for use with a clamping mechanism can include a flexible enclosure having a first end configured for sealing against a limb and a second end adapted to form an access port. The second end can be coupled to an elongated member adapted for releasably coupling to a clamping mechanism for sealing and unsealing the access port.

In still another embodiment of the present invention, a wound treatment device can include a flexible enclosure, having an interior, a first end configured for sealing against a limb, a second end forming a sealable and unsealable access port, and an elongated member about which the second end of the enclosure is coupled thereto. The second end of the elongated member can be adapted to be releasably coupled to a clamping mechanism that can include a first leg, a second leg movable relative to the first leg, an indent disposed on an inside surface of at least one of the first and the second legs to accommodate the elongated member and second end of the enclosure coupled thereto, and a fastener for releasably coupling the first leg to the second leg with the elongated member therebetween.

Embodiment B

In an embodiment of the present invention, a wound treatment device can include a housing having a first open end for receiving a limb of a patient and a second closed end forming a chamber therebetween, wherein a portion of the housing can include a first polymer material coated with a second polymer material selected from the group consisting of ethyl vinyl acetate and polyethylene heat sealable material.

In another embodiment of the present invention, a wound treatment device can include a flexible housing having a wall formed of nylon coated with ethyl vinyl acetate. The housing can further include a first closed end, a second end remote from the first end having an inflatable cuff for sealing against a limb, and a treatment chamber disposed between the first and second ends for accommodating a treatment gas.

In still another embodiment, a method of making a wound treatment device can include providing a first sheet, and a second sheet overlying the first sheet, and manipulating the first and second sheets into a housing having a generally cylindrical configuration, the housing having a first end and a second end remote therefrom. Further, the method can include sealing edges of the first and second sheets along longitudinal edges of the first and second sheets, sealing the first end of the first and second sheets together to form an enclosed first end, and forming a cuff at the second end for sealing against a limb. As will be more fully described below, the wound treatment device 10B is portable and optionally, disposable. In the illustrated embodiment, device 10B is a wound treatment device for enclosing a limb and treating a wound or lesion on the limb with treatment gases. Treatment gas can include oxygen or the like.

In still another embodiment of the present invention, a method of manufacturing a wound treatment device can include providing two sheets of polymer material, folding the two sheets along a symmetrical axis, coating portions of the two sheets with a heat sealable material selected from the group consisting of ethyl vinyl acetate and polyethylene, and heat sealing the two sheets along a portion of their perimeter to form an enclosure. The enclosure can have a closed end and an open end, having an interior between the open and closed ends for accommodating a treatment gas.

Embodiment C

In an embodiment of the present invention, a wound treatment device can include a housing having a closed end and an open end configured to seal against a limb, and at least two compartments within the housing separated by a divider cuff configured to seal against the limb.

In another embodiment of the present invention, a wound treatment device can include a housing having a closed end and an open end configured to seal against a limb, and a plurality of separate compartments within the housing divided by a plurality of inflatable divider cuffs configured to seal against the limb. Each of the inflatable divider cuffs can be coupled to a valve for inflation.

In still another embodiment of the present invention, a wound treatment device can include a housing having a closed end and an open end configured to seal against a limb, and at least two compartments separated by an inflatable divider cuff having an opening for receiving a limb. The housing can be configured for at least one treatment selected from hyperbaric gas treatment, sequential compression treatment, and evacuation treatment.

Embodiment D

In an embodiment of the present invention, a wound treatment device can include a housing for the treatment of a limb of a patient by a gas supplied thereto, a housing pressure sensor for measuring a pressure in the housing, an inflatable cuff for sealing the housing against the limb of the patient. The cuff can include a cuff gas inlet valve, a cuff gas outlet valve, and a controller for opening and closing the cuff gas inlet and outlet valves. The controller can adjust the supply of gas into the cuff for controlling the cuff pressure based on measurements of the housing pressure as determined by the housing pressure sensor.

In another embodiment of the present invention, a wound treatment device can include a housing for treatment of a limb of a patient by a gas supplied thereto, an inflatable cuff for sealing the housing against the limb of a patient, and a controller for controlling a cuff pressure by inflating or deflating the cuff responsive to a gas pressure in the housing.

In yet another embodiment of the present invention, a wound treatment device can include a housing having an interior, an interior pressure sensor for measuring a pressure in the interior, and an inflatable cuff for sealing a limb within the interior of the housing. The cuff can include a cuff valve in fluid communication with an inflating gas source and a cuff pressure sensor for measuring a gas pressure within the cuff. The device can include a control system for controlling the pressure in the cuff by operation of the cuff valve, responsive to the interior pressure sensor.

In still another embodiment of the present invention, a method for creating a seal about a patient's limb in a wound treatment device can include inflating a cuff seal about the patient's limb to a first pressure, monitoring a gas pressure in the device, and controlling the gas pressure in the cuff seal responsive to the gas pressure in the device.

BRIEF DESCRIPTION OF THE DRAWINGS

The various objects, advantages and features of this invention will be more fully apparent from a reading of the following detailed description in conjunction with the accompanying drawings in which like reference numerals refer to like parts, and in which.

Embodiment A

Embodiment B

Figure 1A:
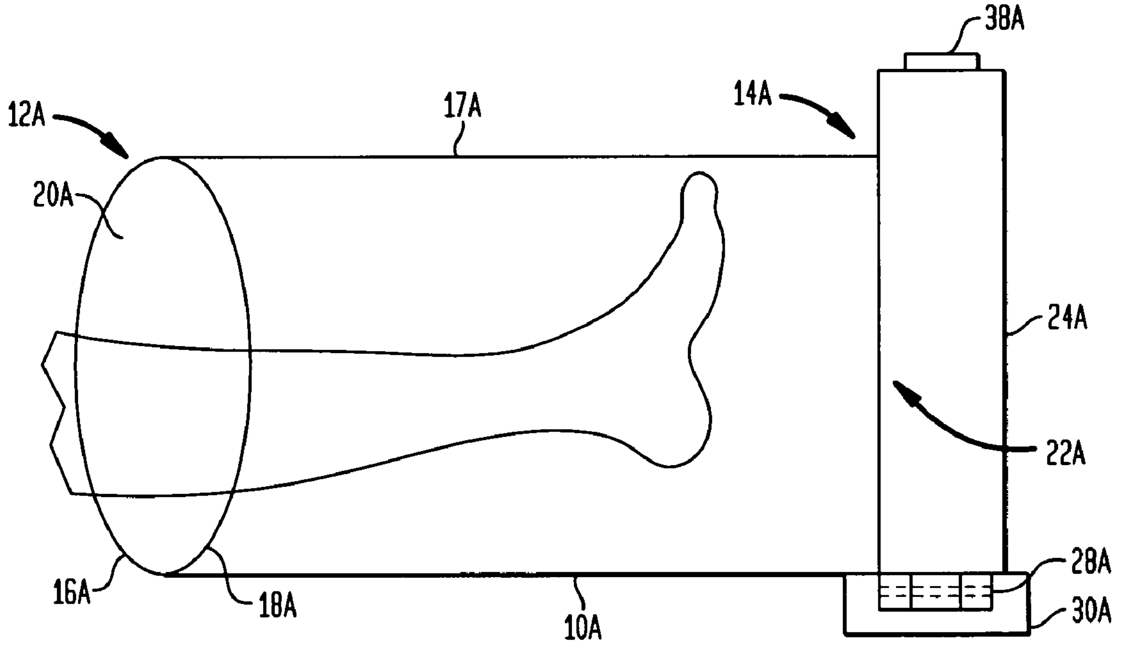
FIG. 1A is a schematic view of a wound treatment device coupled to a clamping mechanism according to an embodiment of the present invention.
Figure 1B:
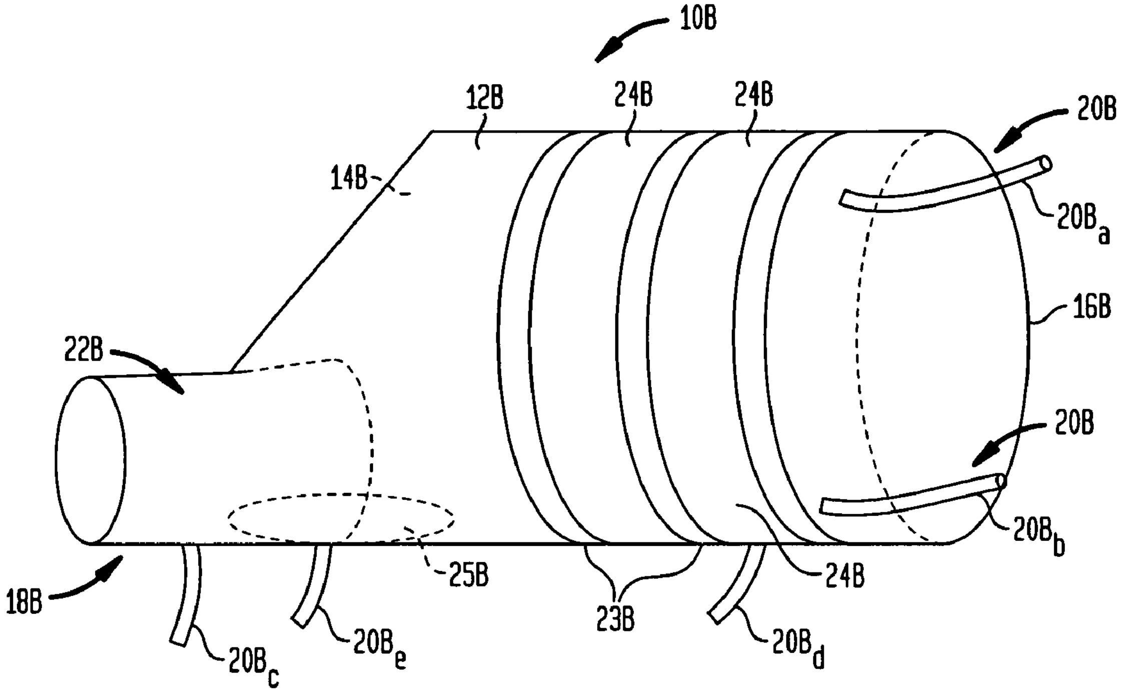

FIG. 1B is a perspective view of a wound treatment device according to an embodiment of the present invention.

Figure 2A:
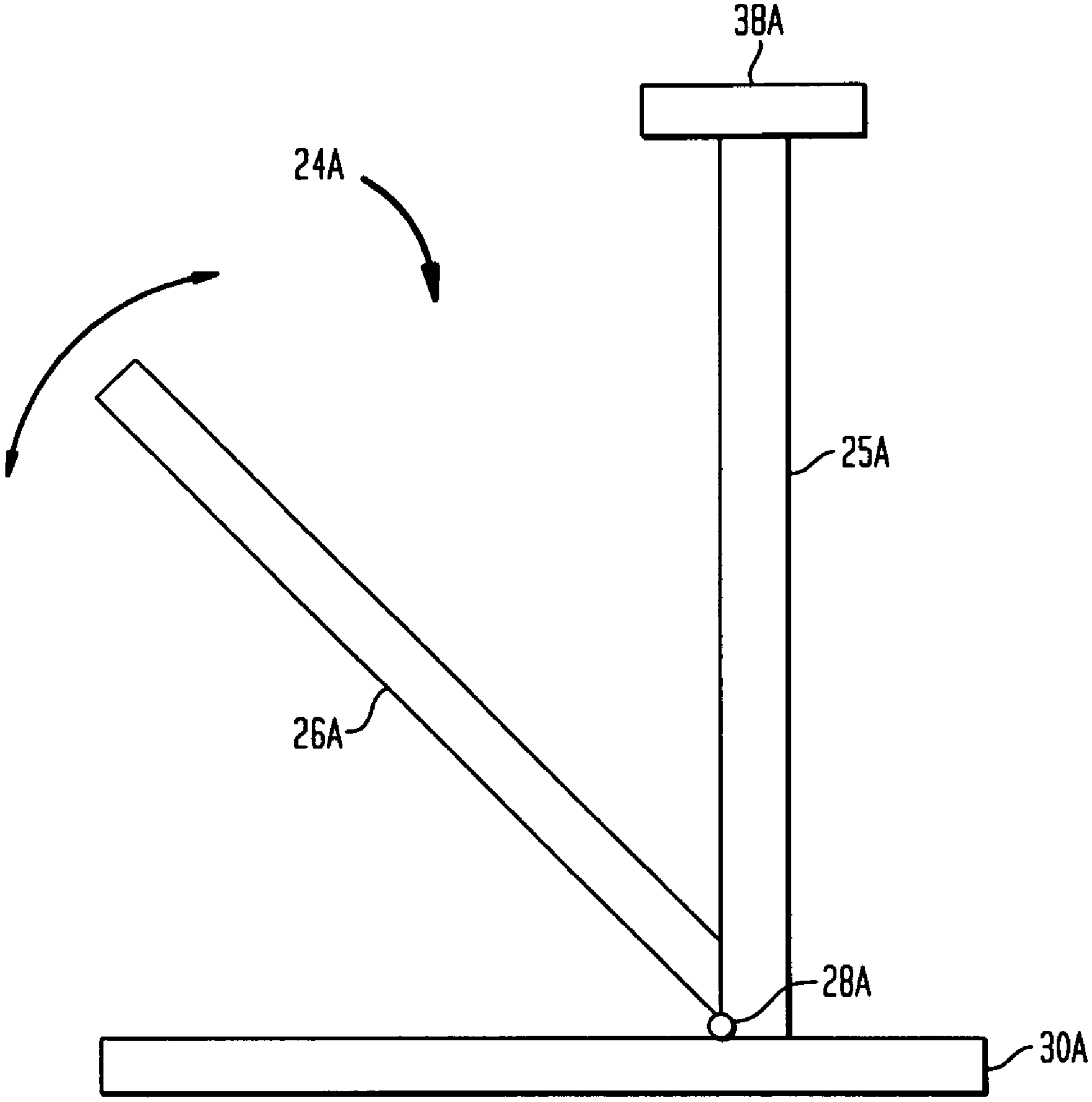
FIG. 2A is a side view of the clamping mechanism of FIG. 1A.
Figure 2B:
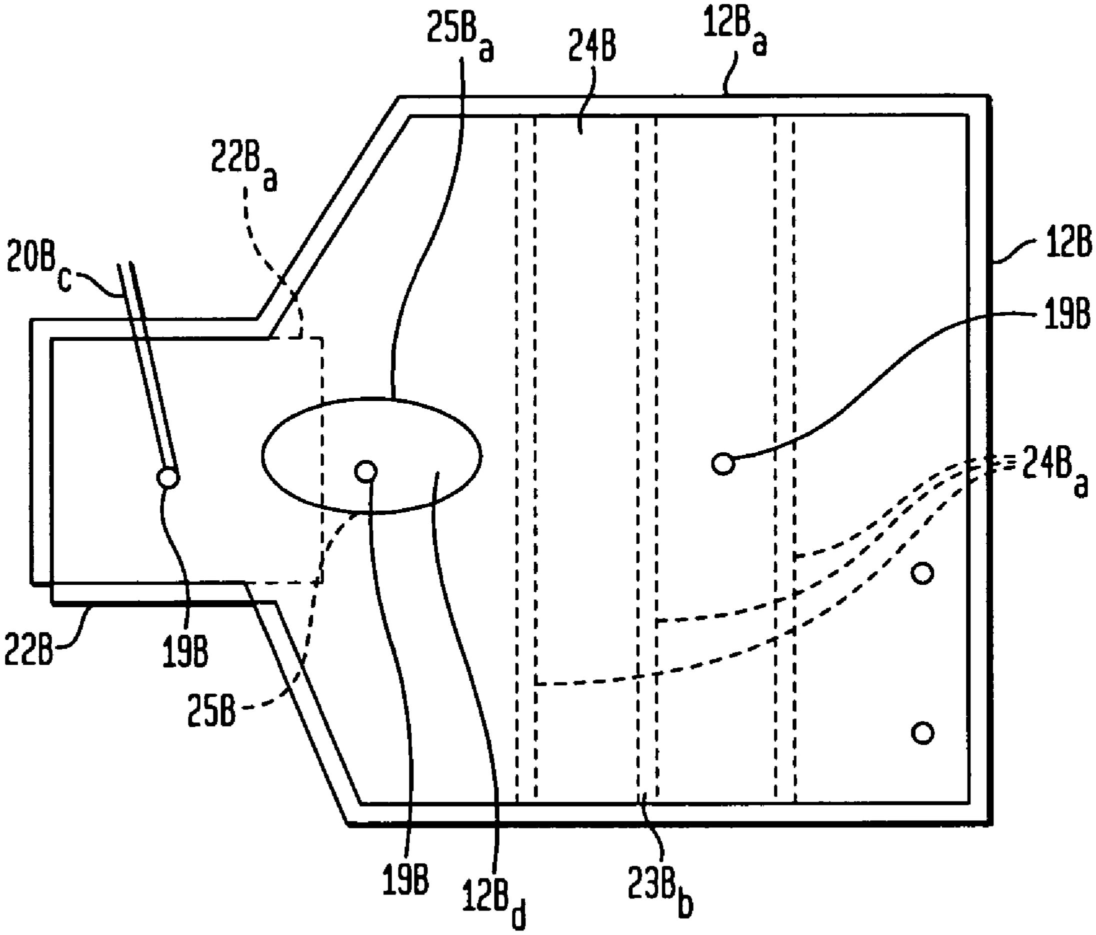

FIG. 2B is a plan view of a first step for forming the wound treatment device of FIG. 1B.

Figure 3A:
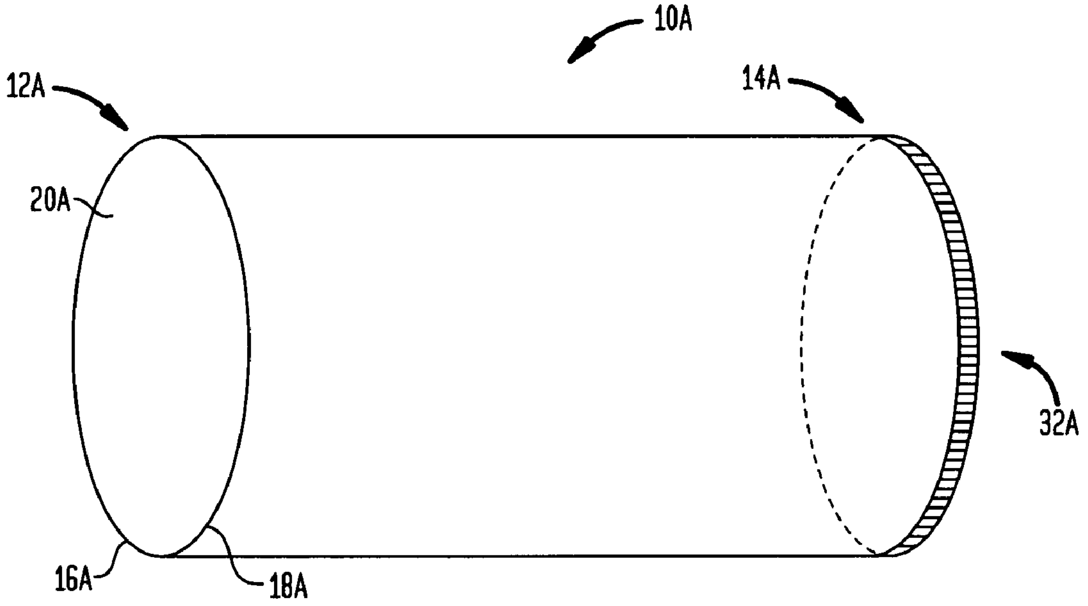
FIG. 3A is a front perspective view of the wound treatment device configured for the clamping mechanism of FIG. 1A.
Figure 3B:
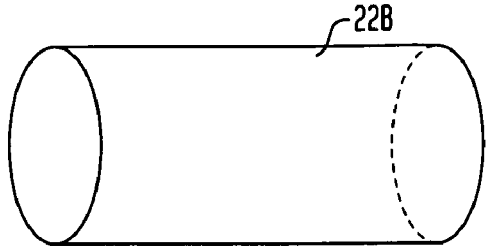
Figure 3B:
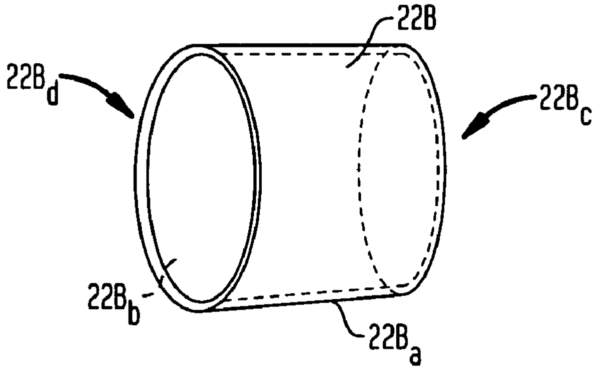
Figure 3B:
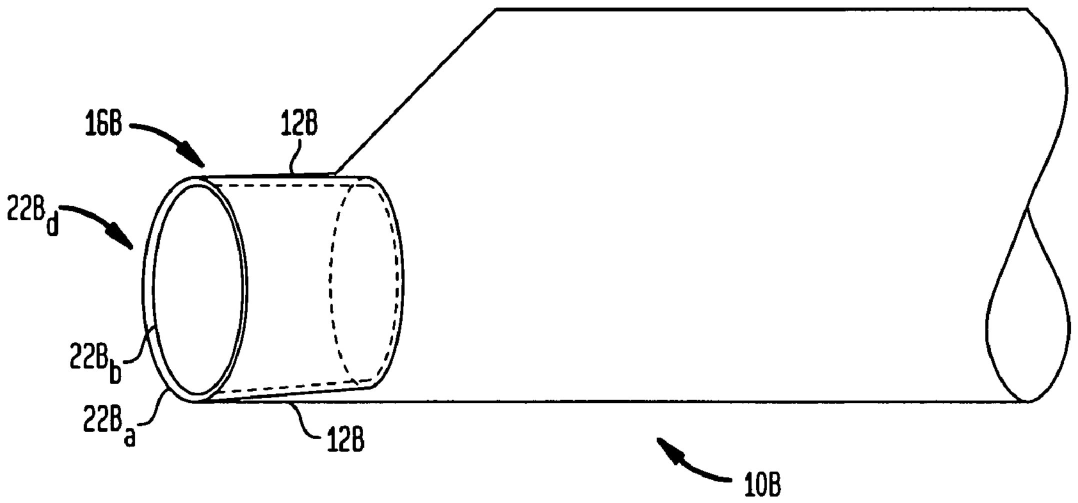

FIGS. 3Ba, 3Bb and 3Bc are perspective views for forming a cuff seal of the wound treatment device of FIG. 1B.

Figure 4A:
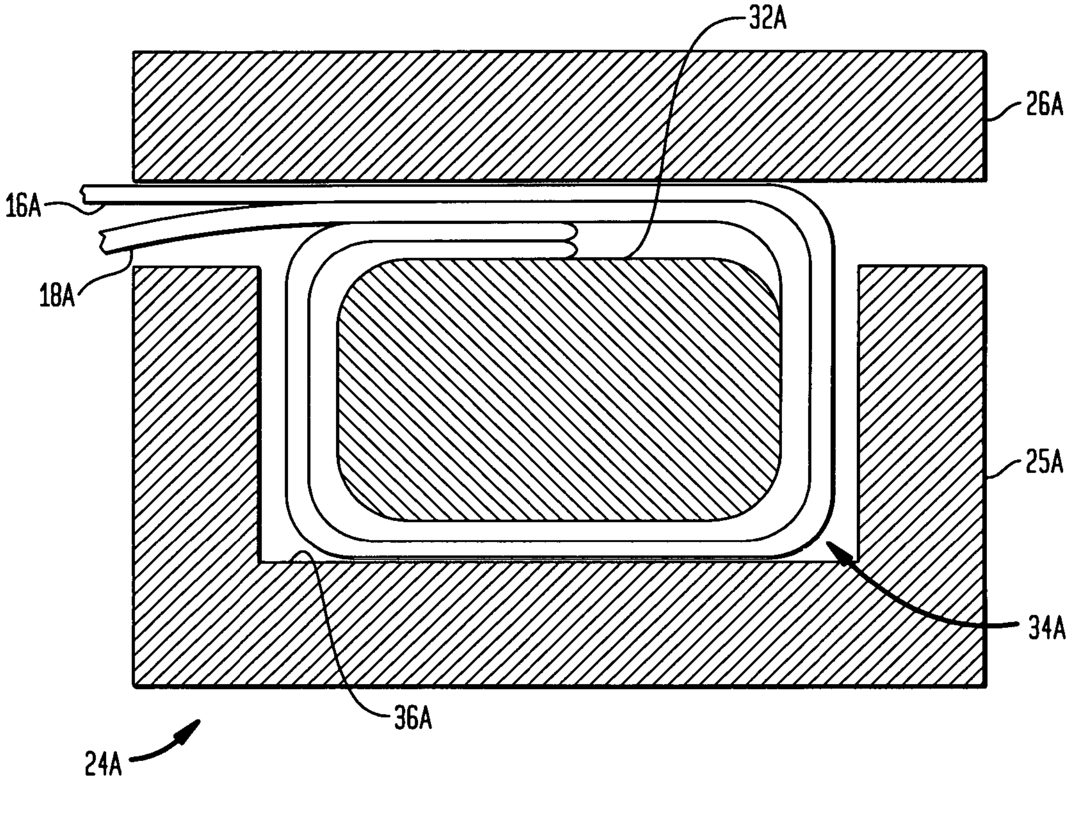
FIG. 4A is a top plan view of a sealed access port.
Figure 4B:
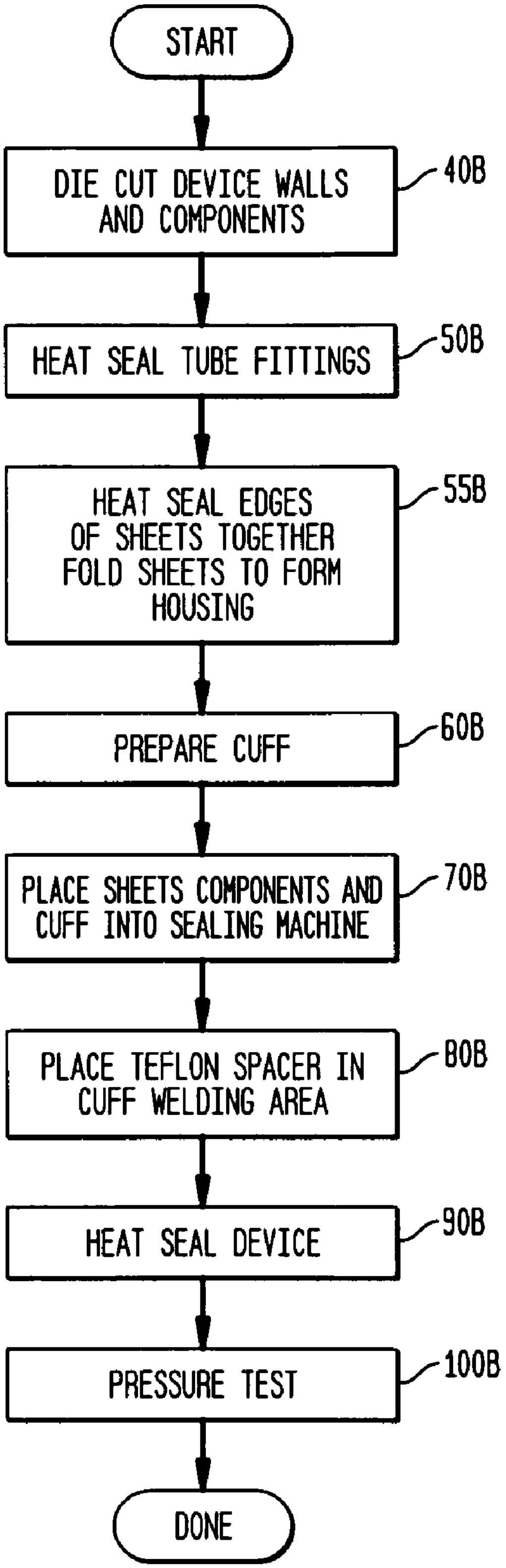

FIG. 4B is a flowchart of the manufacturing steps required to construct the wound treatment device according to one embodiment of the present invention.

Figure 5A:
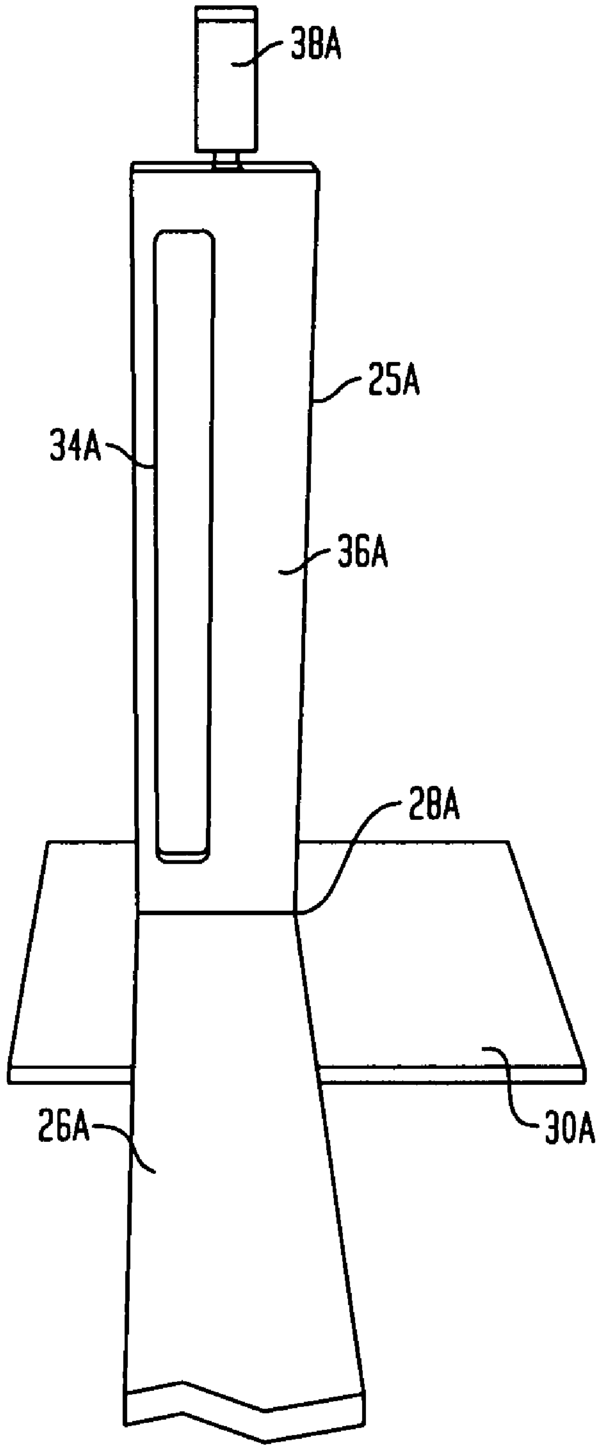
FIG. 5A is a front view of the clamping mechanism in an open position.
Figure 5B:
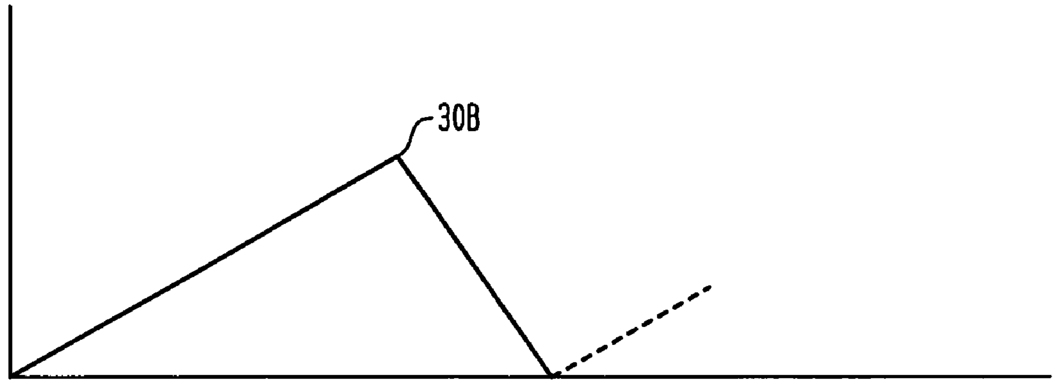

FIG. 5B is a pressure waveform diagram from a wound treatment device according to one embodiment of the present invention.

Figure 6A:
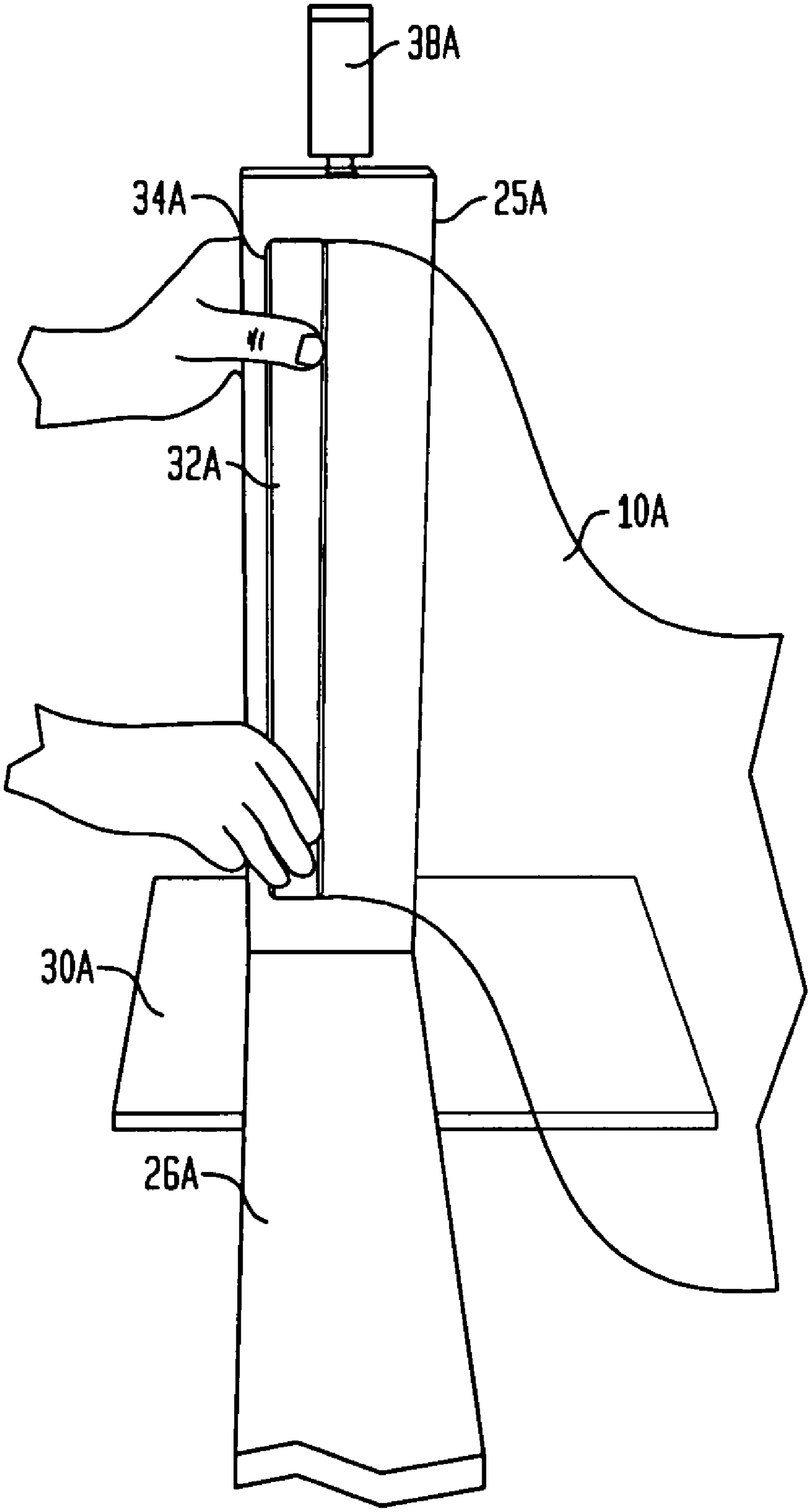
FIG. 6A is a front view of the wound treatment device and the clamping mechanism in an open position.
Figure 6B:
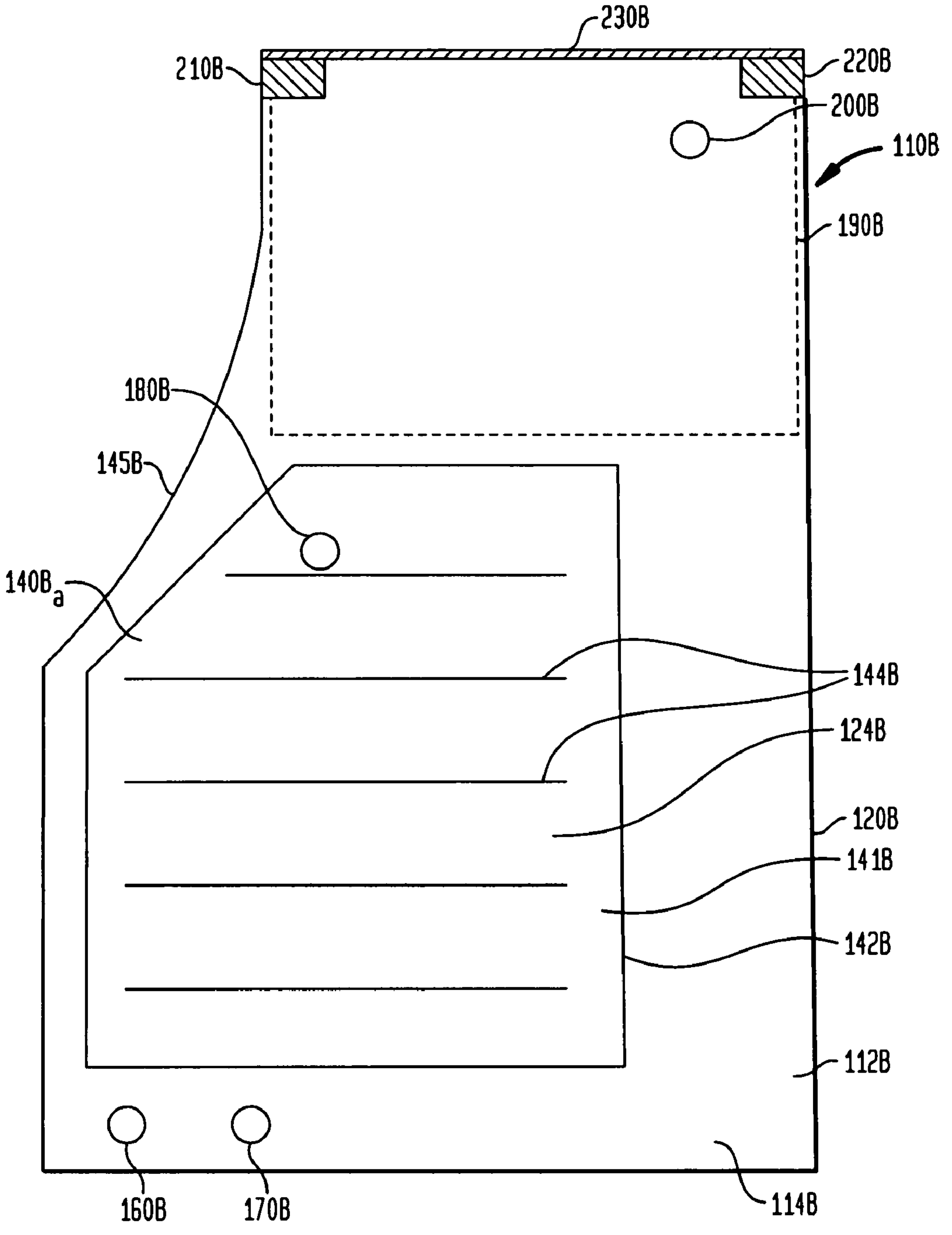

FIG. 6B is a cross sectional view of a wound treatment device according to another embodiment of the present invention.

Embodiment C

Figure 1C:
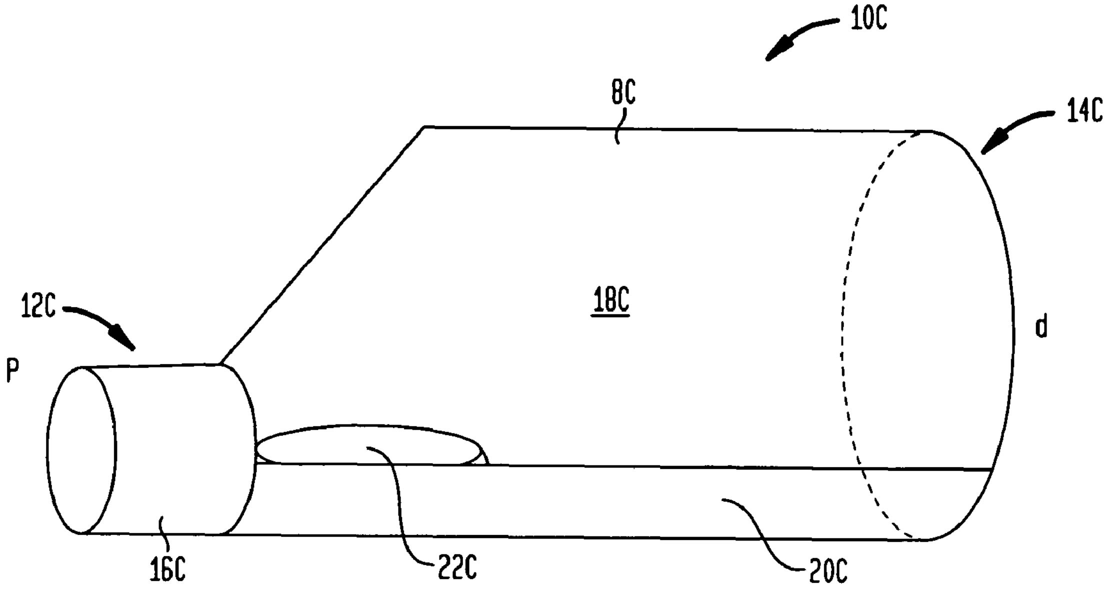

FIG. 1C is a perspective view of a wound treatment device according to an embodiment of the present invention.

Figure 2C:
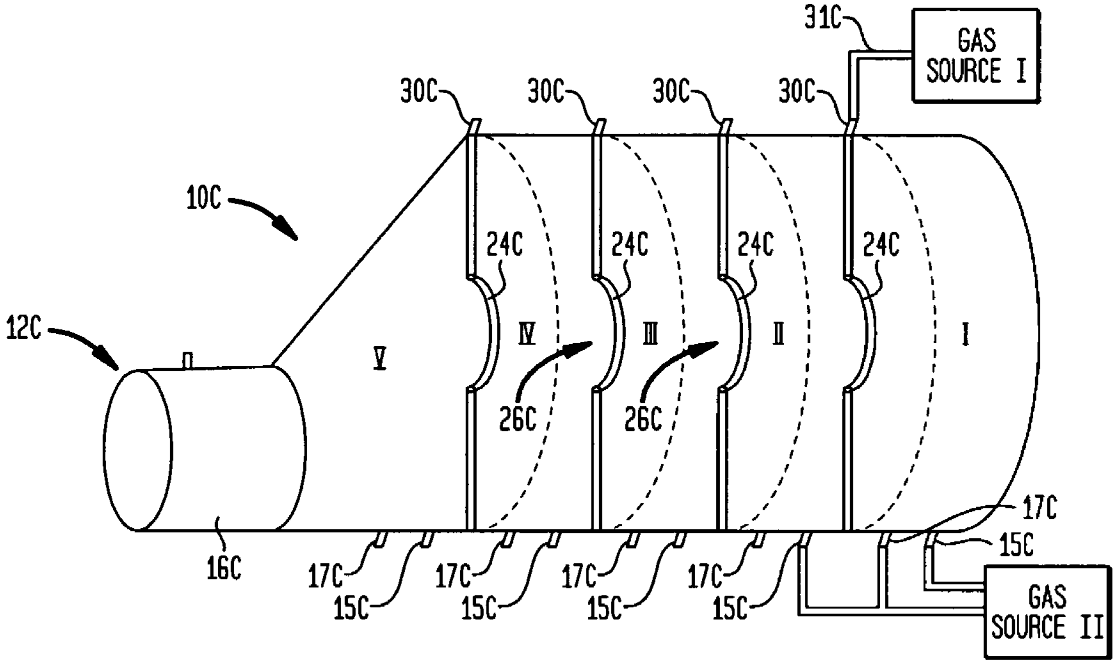

FIG. 2C is a cross sectional view of the device of FIG. 1C.

Figure 3C:
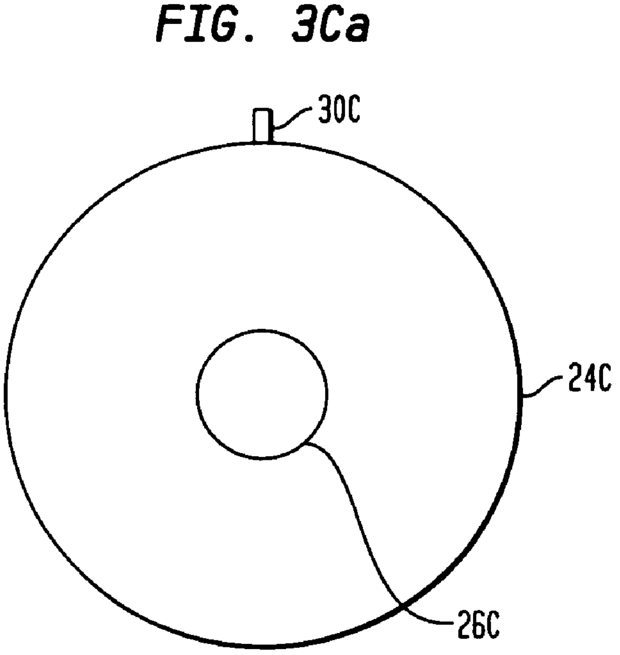
Figure 3C:
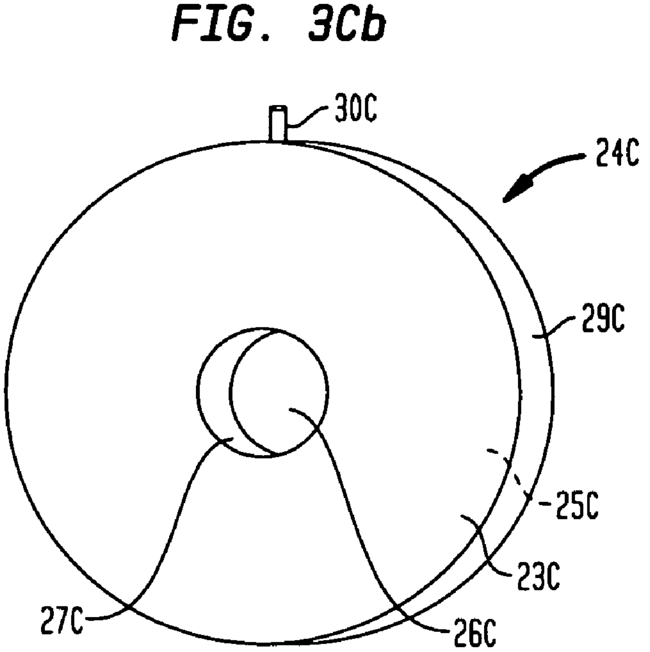

FIGS. 3Ca-3Cb are views of a divider cuff according to an embodiment of the present invention.

Figure 4C:
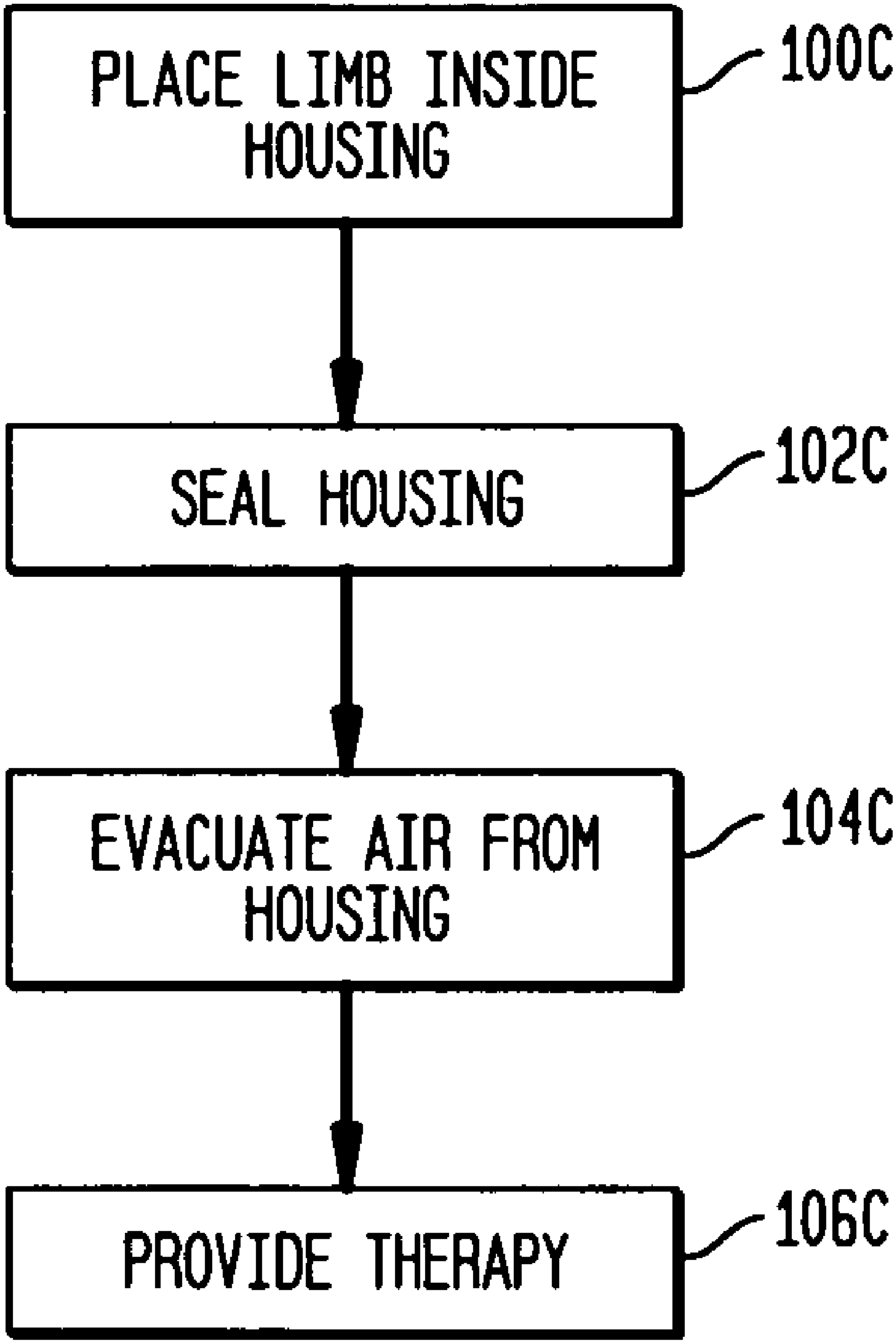

FIG. 4C is a method of utilizing the device in an embodiment of the present invention.

Figure 5C:
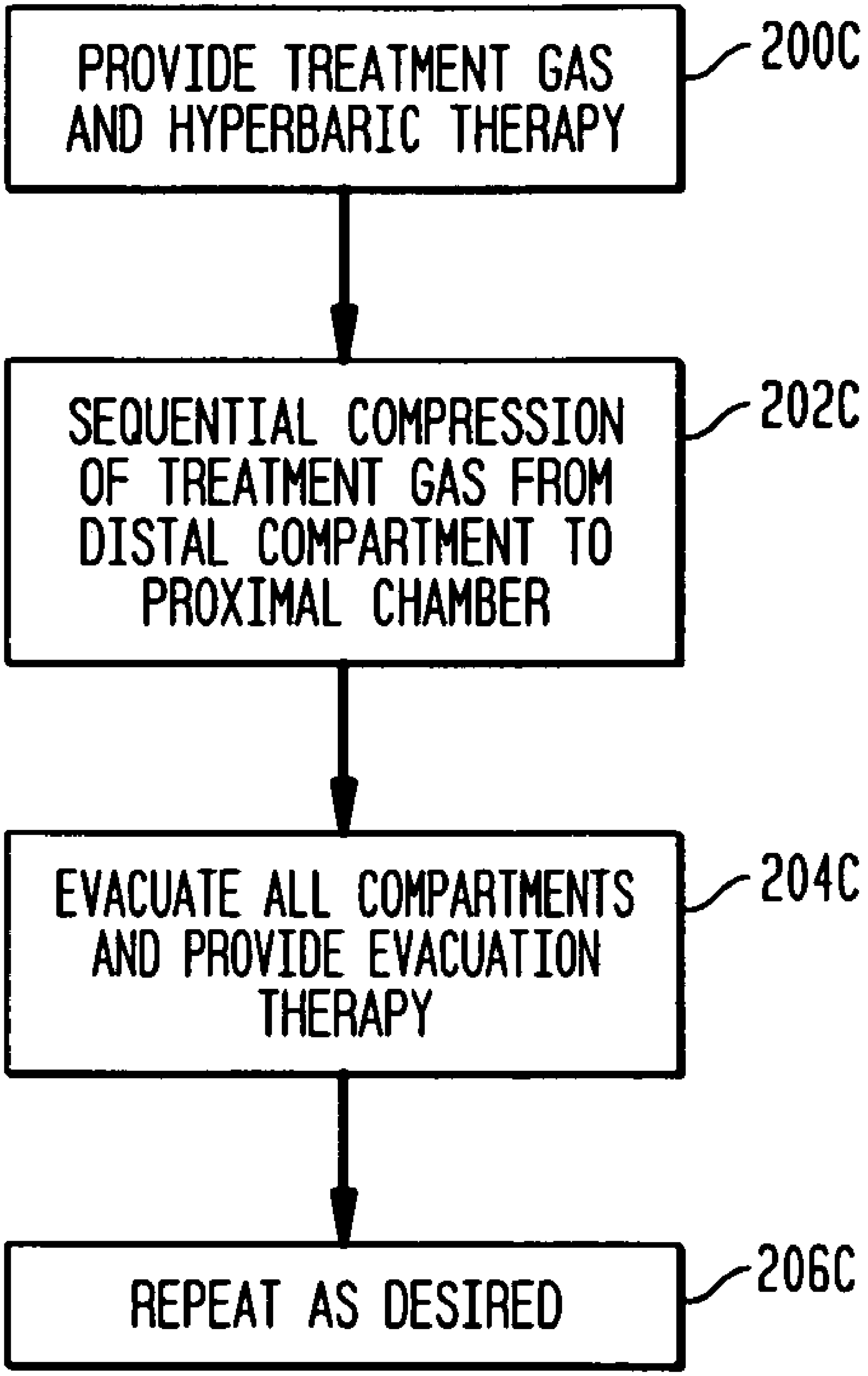

FIG. 5C is an exemplary cycle performed by the device according to an embodiment of the present invention.

Figure 6C:
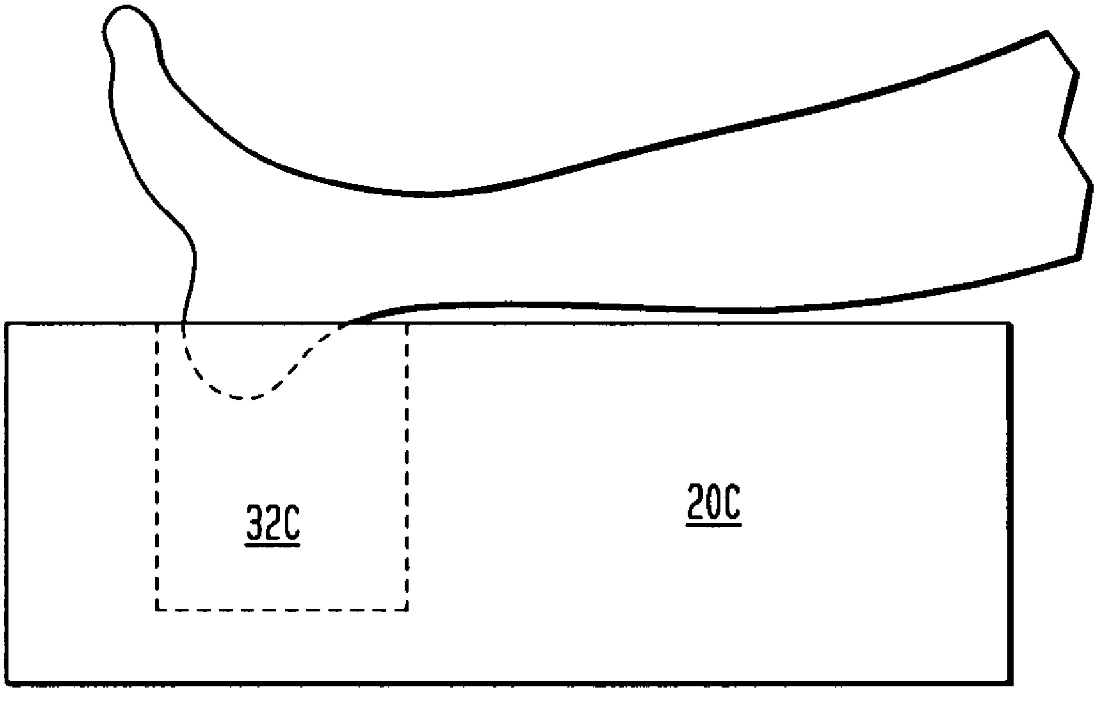

FIG. 6C is an absorbent liner device according to another embodiment of the present invention.

Embodiment D

Figure 1D:
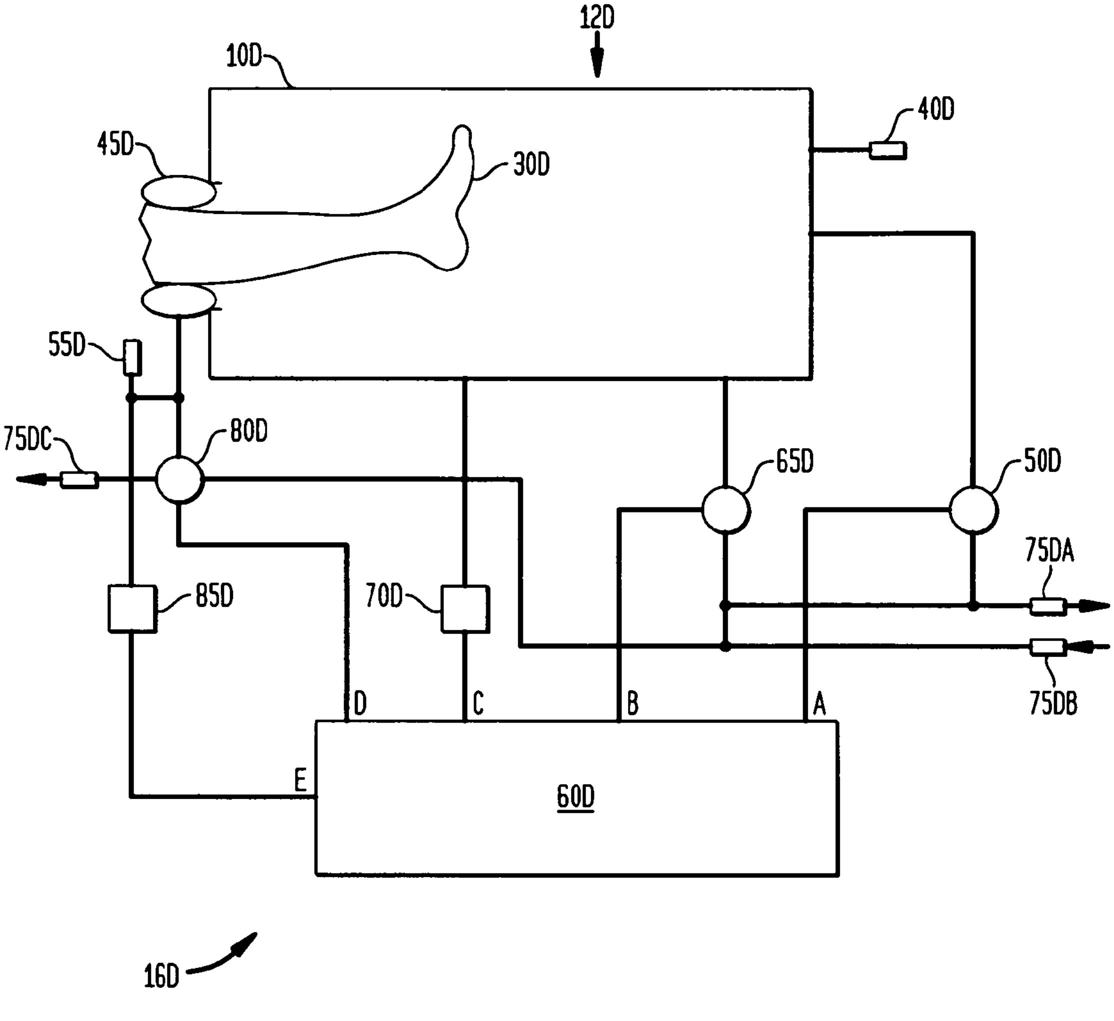

FIG. 1D is a schematic diagram of a wound treatment device according to an embodiment of the present invention.

Figure 2D:
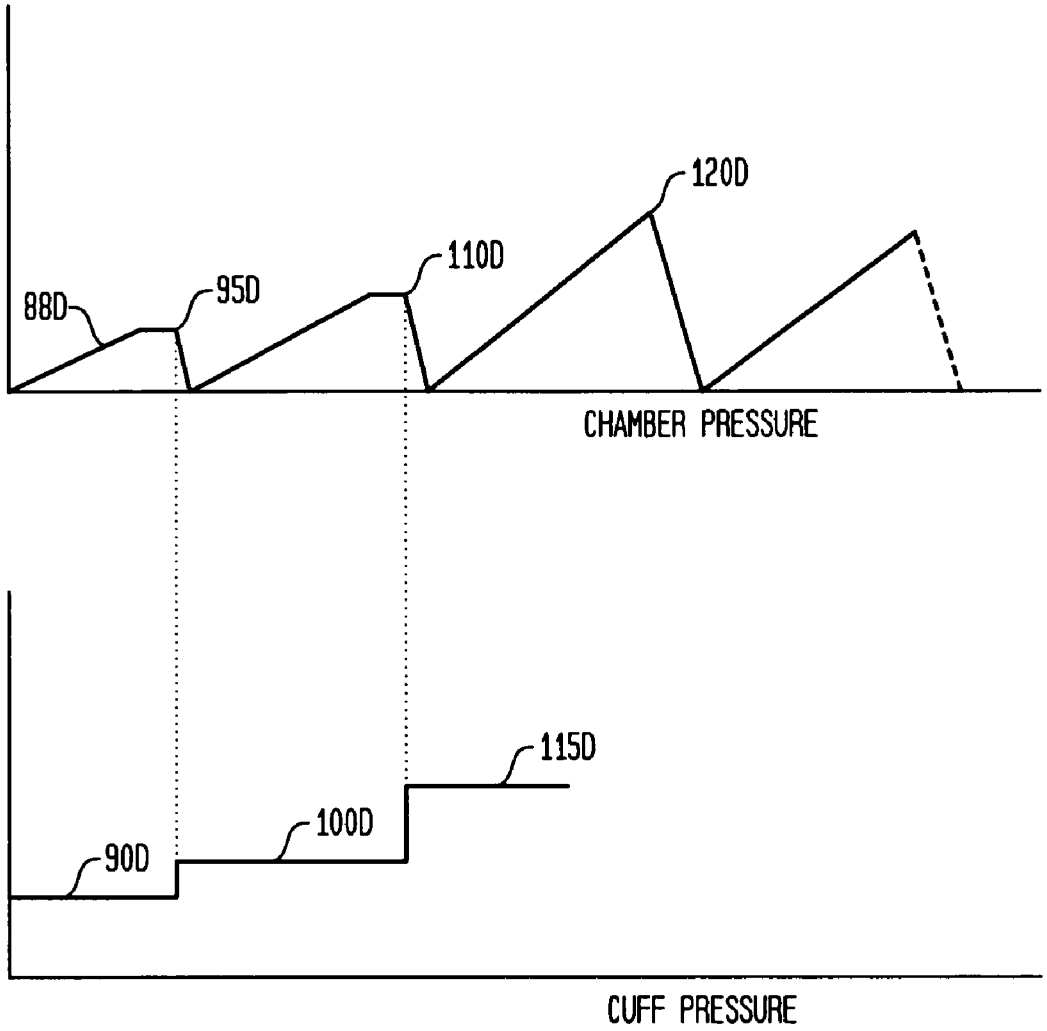

FIG. 2D is a timing diagram for an operation of the device of FIG. 1D.

Figure 3D:
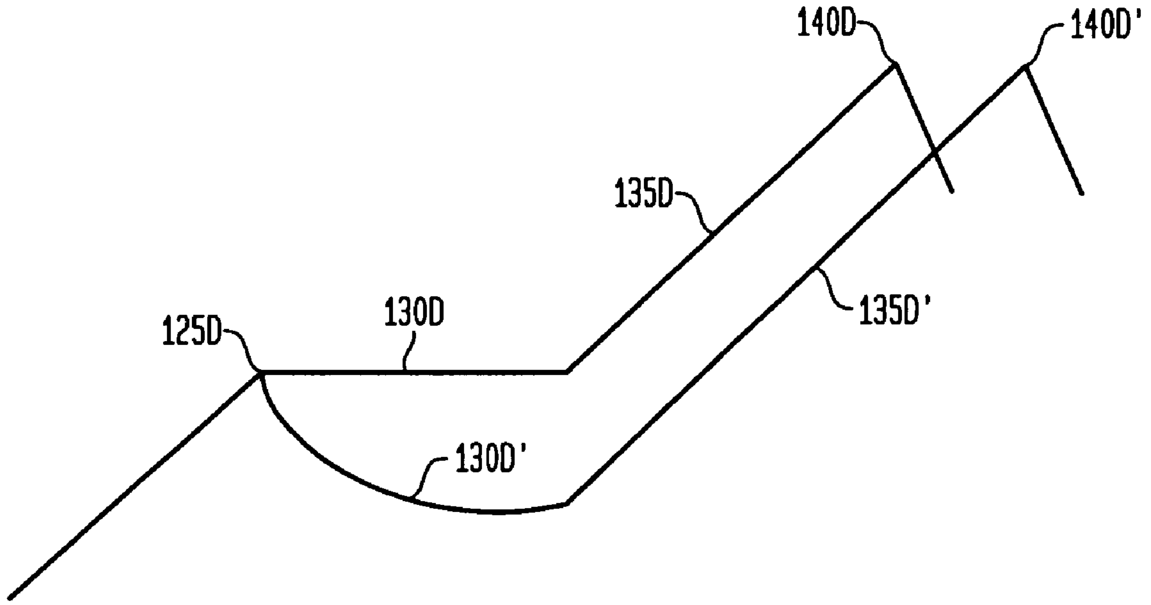

FIG. 3D is a partial timing diagram for the operation of the device of FIG. 1D.

Figure 4D:
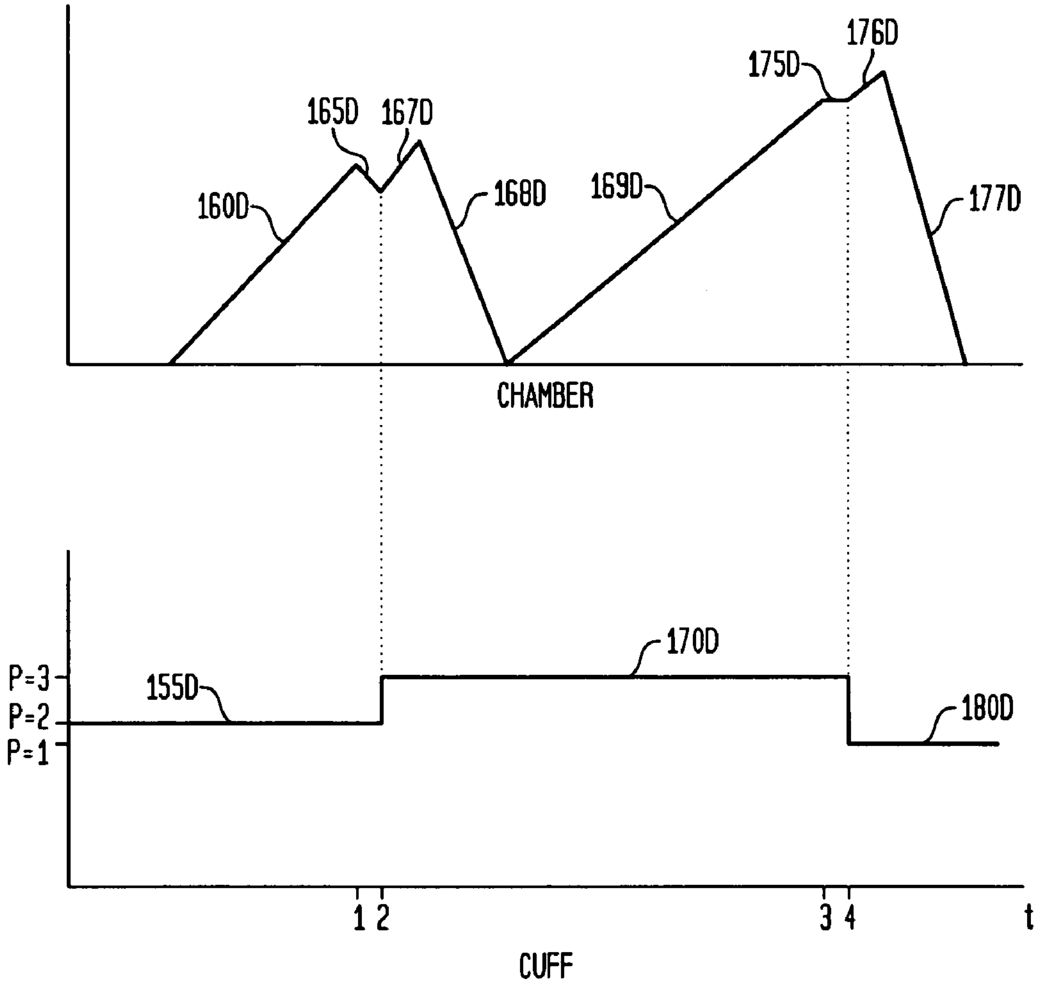

FIG. 4D is a complete timing diagram for the operation of the device of FIG. 1D in an embodiment of the present invention.

Figure 5D:
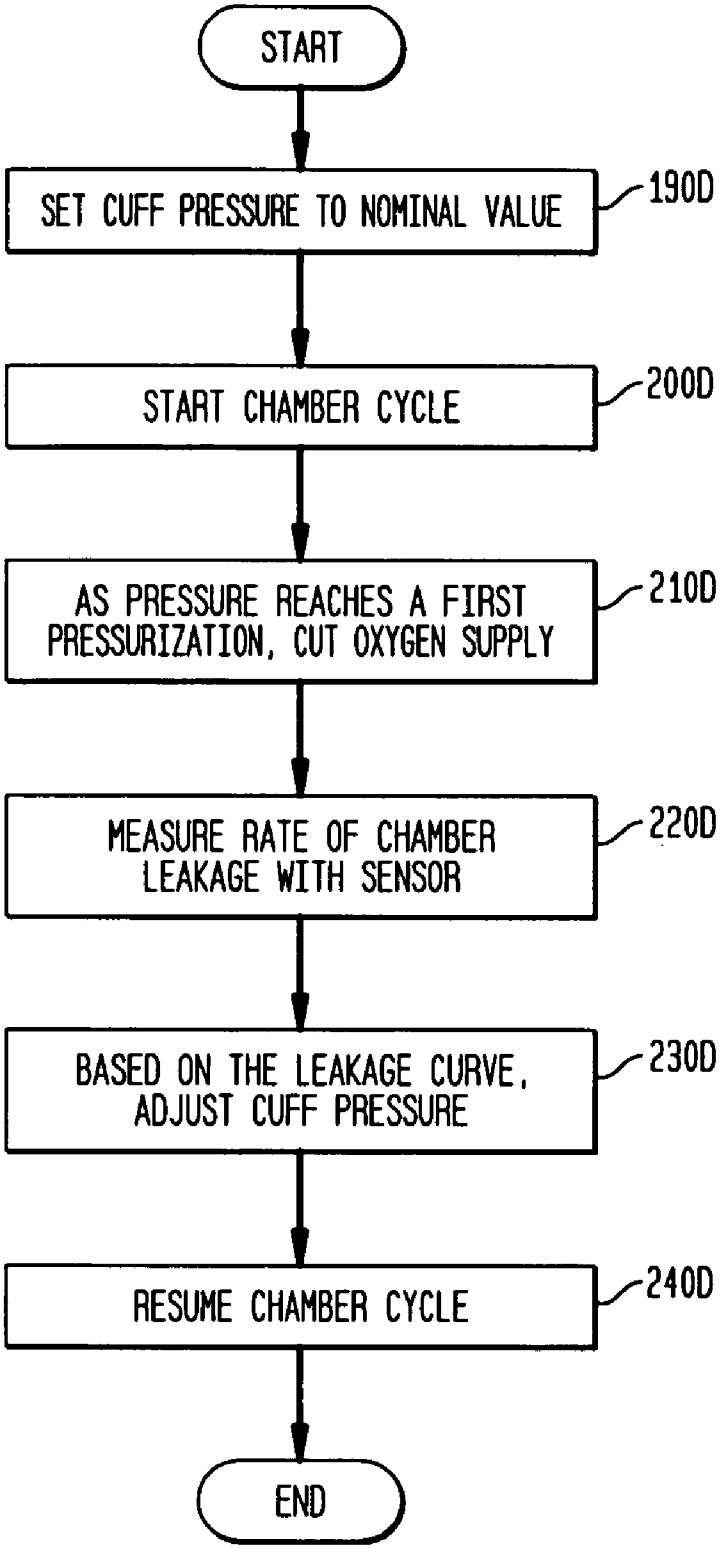

FIG. 5D is a flow chart of an operation of the device of FIG. 1D according to an embodiment of the present invention.

Figure 6D:
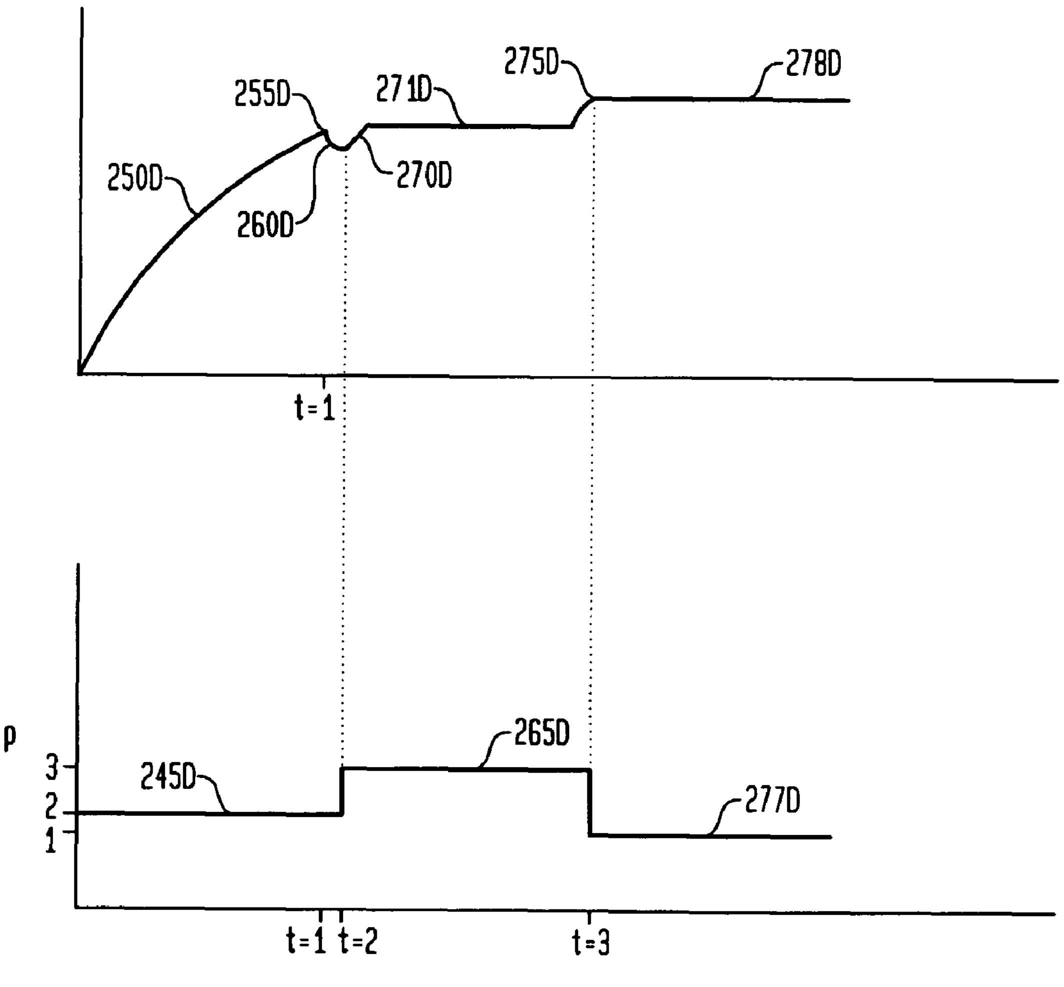

FIG. 6D is a timing diagram of another operation of the device according to another embodiment of the present invention.

DETAILED DESCRIPTION

Numerous embodiments related to wound treatment devices are disclosed herein. Generally, wound treatment devices are used to hasten wound healing using a treatment gas such as oxygen. Further, the embodiments disclosed herein relate to devices having a flexible housing, although a rigid housing can easily be incorporated. In addition, wound treatments include hyperbaric therapy, compression therapy and evacuation therapy. As will be more fully described below, the wound treatment device is portable and optionally, disposable.

Embodiment A

In an embodiment of the present invention, a flexible wound treatment device includes an access port. The access port allows a clinician to easily access the limb being treated and adjust the limb. Further, the clinician can apply medication or change dressings in a manner similar to that attained with the prior art rigid chamber access ports.

FIG. 1A illustrates a flexible wound treatment device having an access port and a corresponding clamping mechanism. In particular, a flexible wound treatment device 10A includes a first end 12A that receives a limb and a second end 14A that includes an access port. The first end 12A can be sealed about the patient's limb by any suitable means. One such sealing means is in the nature of an inflatable cuff to be described hereinafter.

The device 10A generally includes two sheets of materials 16A, 18A that are permanently sealed at ends parallel to the longitudinal axis to form an interior 20A of the device 10A. The sheets 16A, 18A can be formed of polymer materials or any other suitable material that can facilitate inflation and which are typically impermeable to the treatment gas. Alternatively, the device 10A may be formed of a single sheet folded over and permanently sealed at a side 17A between the first and second ends 12A, 14A, respectively. In that instance, sheets 16A, 18A refer to a side of the folded single sheet. A limb is inserted into the interior 20A formed by the two sheets 16A, 18A through the open first end 12A. The two sheets 16A, 18A are releasably sealed together adjacent the second end 14A. Sealing and unsealing of the two sheets 16A, 18A, at the second end 14A forms an access port 22A.

As shown in FIGS. 1A and 2A, a clamping mechanism 24A is used to seal and unseal the second end 14A to provide the access port 22A. The clamping mechanism 24A includes an elongated first leg 25A and an elongated second leg 26A. A hinge 28A is disposed between the first and second legs 25A, 26A to allow one leg to move pivotably relative to the other leg. The first and second legs, 25A, 26A and the hinge 28A are supported by a base 30A.

The clamping mechanism 24A can be constructed from a molded resinous material or other medically accepted material such as stainless steel. The clamping mechanism 24A does not contact the interior 20A of the flexible device 10A and therefore, poses little or no infection risk to the patient. This allows the clamping mechanism 24A to be reused as often as desired. Further, the clamping mechanism 24A can be arranged generally vertical, in one embodiment of the present invention, although any suitable configuration may be utilized, such as for example, horizontal or at any desired angle. Although one leg 25A, 26A of the clamping mechanism 24A is movable relative to the other leg, either leg can be moved relative to the other and either leg can remain stationary, as desired. In the vertical configuration, the base 30A is provided to keep the clamping mechanism 24A in an upright position during sealing and unsealing of the access port 22A. The base 30A can be configured to support the clamping mechanism 24A in a horizontal embodiment or in an embodiment where the clamping mechanism is disposed at an angle by laying the clamping mechanism on its side or at an angle.

The second end 14A can include an elongated member such as a slat 32A to facilitate coupling the clamping mechanism to the second end. The slat 32A is attached, either fixedly or removably, to one of the sheets of the device adjacent its second end 14A. In the example shown at FIG. 3A, the slat 32A is shown affixed to the second sheet 18A, although it may be affixed to the first sheet 16A. The slat 32A is generally as long as or longer than the length of the second end 14A of the device 10A. The slat 32A can be constructed from a resinous material such as plastic, steel or other medically acceptable material. Thus, the slat may be flexible or rigid.

The slat 32A is an elongated member that is either affixed to one of the sheets at the second end 14A or can be provided separately. Preferably, the slat 32A includes ribs, a roughened surface, or the like, to allow the sheets to grip the slat. However, ribs, a roughened surface, or the like is not necessary. Generally, the slat 32A is an elongated member such as a rod or the like, about which the second end 14A of the sheets are rolled. The end of the two sheets of the device 16A, 18A are brought together and are wrapped around the slat 32A and placed within the clamping mechanism 24A, as shown in FIG. 4A. These sheets 16A, 18A are wrapped at least once, preferably twice, around the slat 32A.

As shown in FIGS. 4A and 5A, an elongated indent 34A can be formed on an inside surface 36A of the first leg 25A to accommodate the slat 32A and the rolled sheets 16A, 18A of the device 10A. The indent 34A can be sized according to the size and shape of the slat 32A. The indent 34A may easily be formed on an inside surface of the second leg or an indent may be formed on the inside surfaces of both legs to accommodate the slat 32A and the rolled sheets 16A, 18A. Any such configuration may be utilized.

Figure 7A:
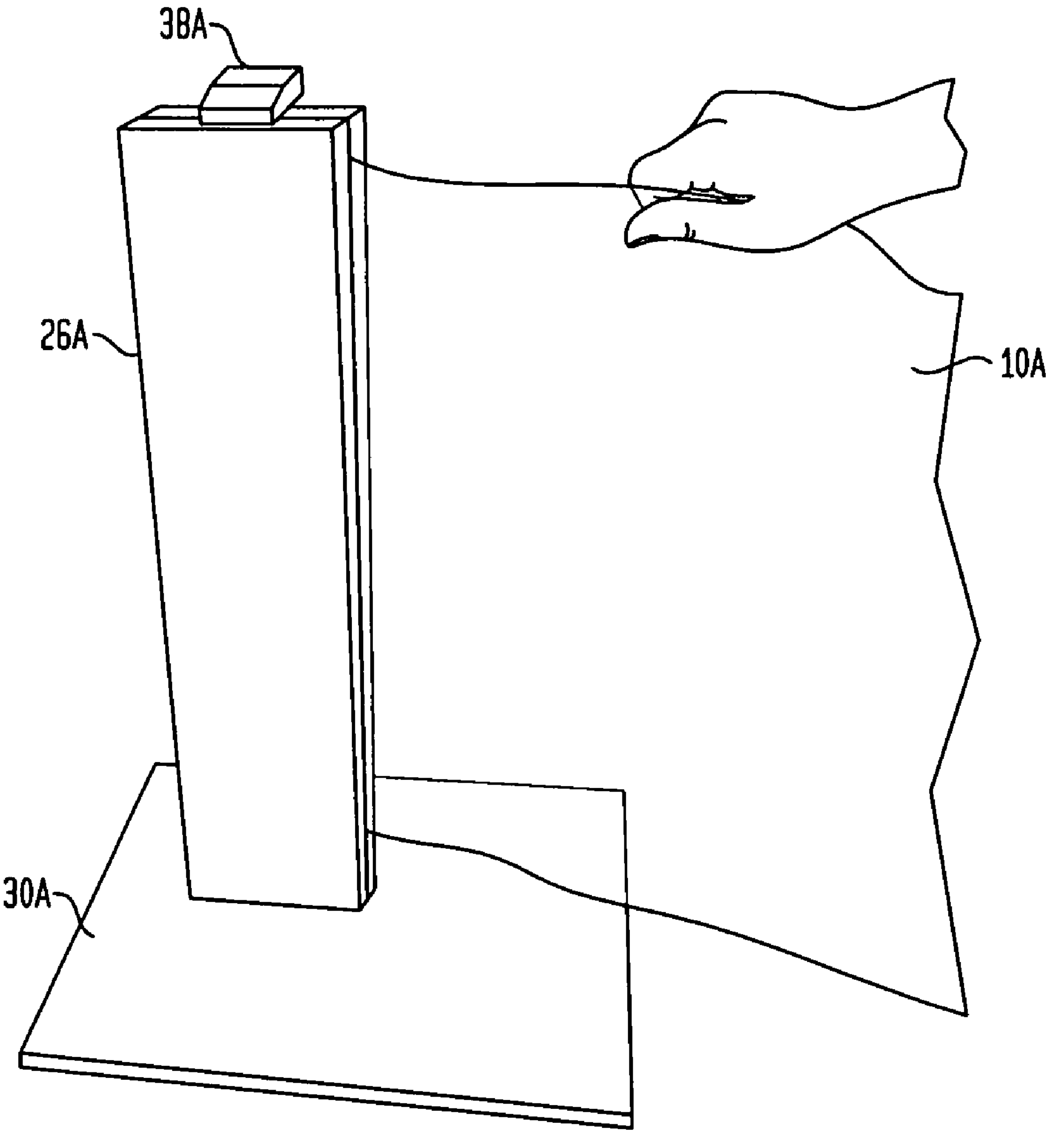
FIG. 7A is a front view of the wound treatment device and the clamping mechanism in a closed position.
Figure 8A:
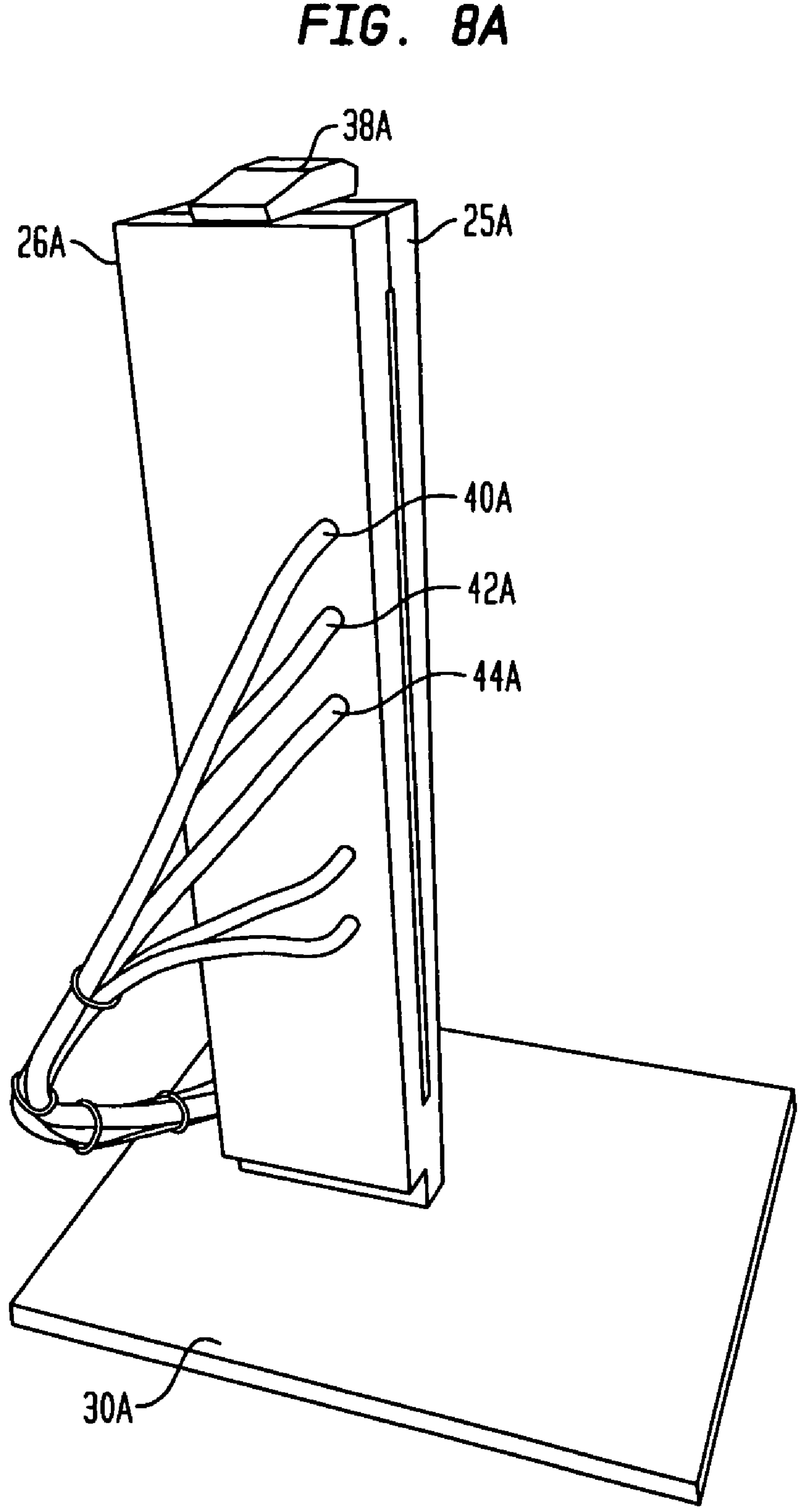
FIG. 8A is a perspective view of another embodiment of the clamping mechanism.
Figure 9A:
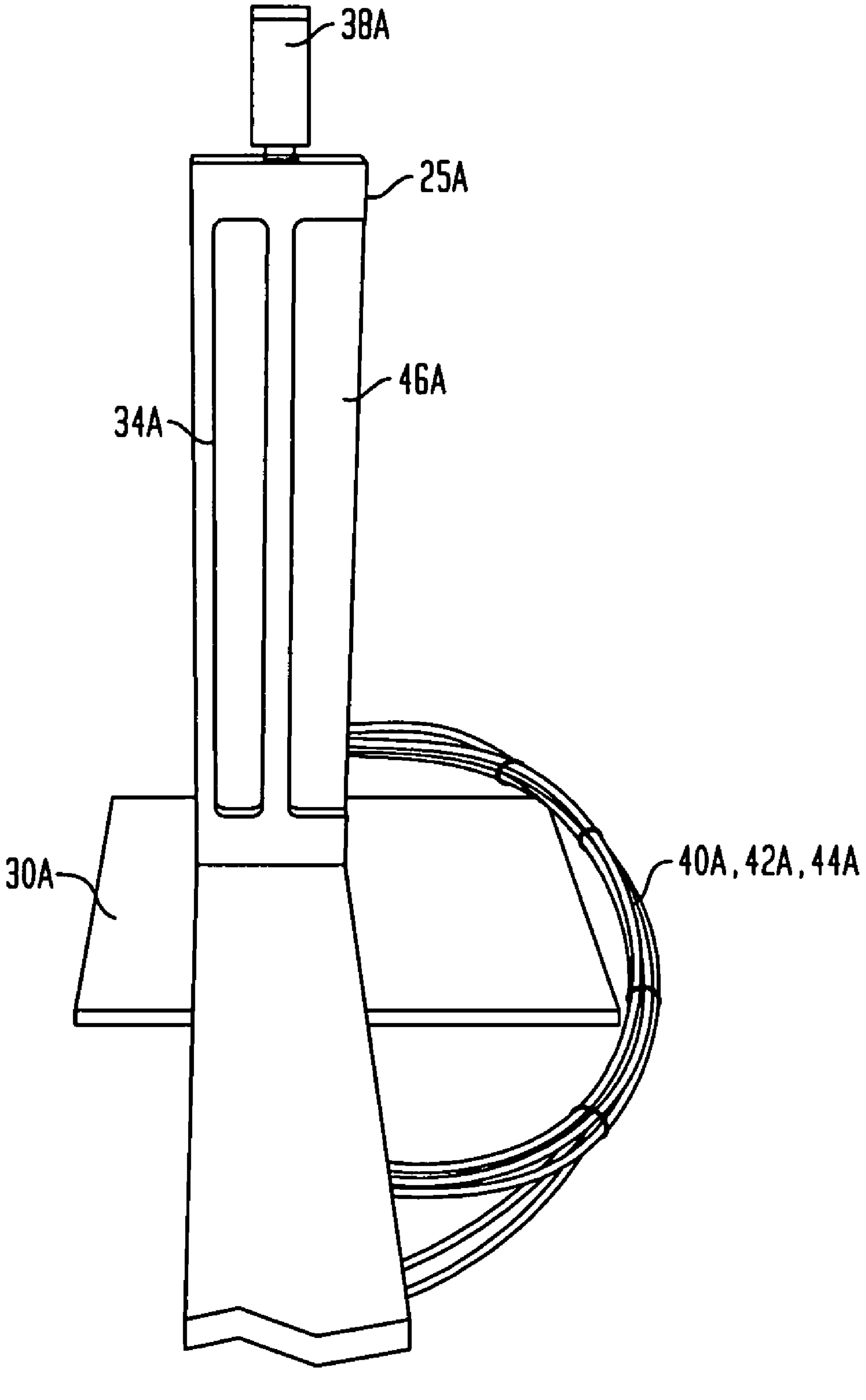
FIG. 9A is a front view of the clamping mechanism of FIG. 8A in an open position.
Figure 10A:
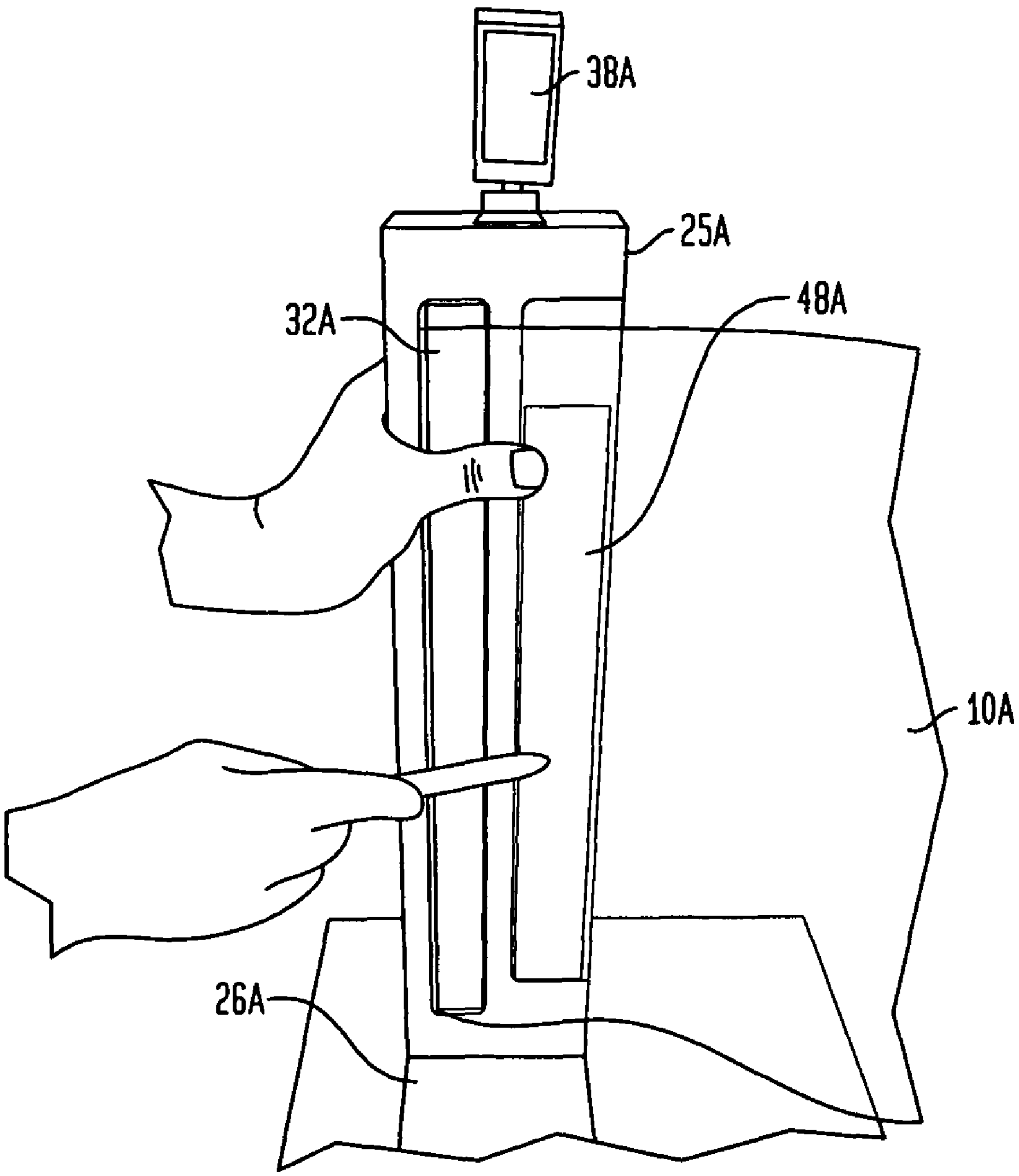
FIG. 10A is a front view of a wound treatment device and the clamping mechanism of FIG. 8A in an open position.
Figure 11A:
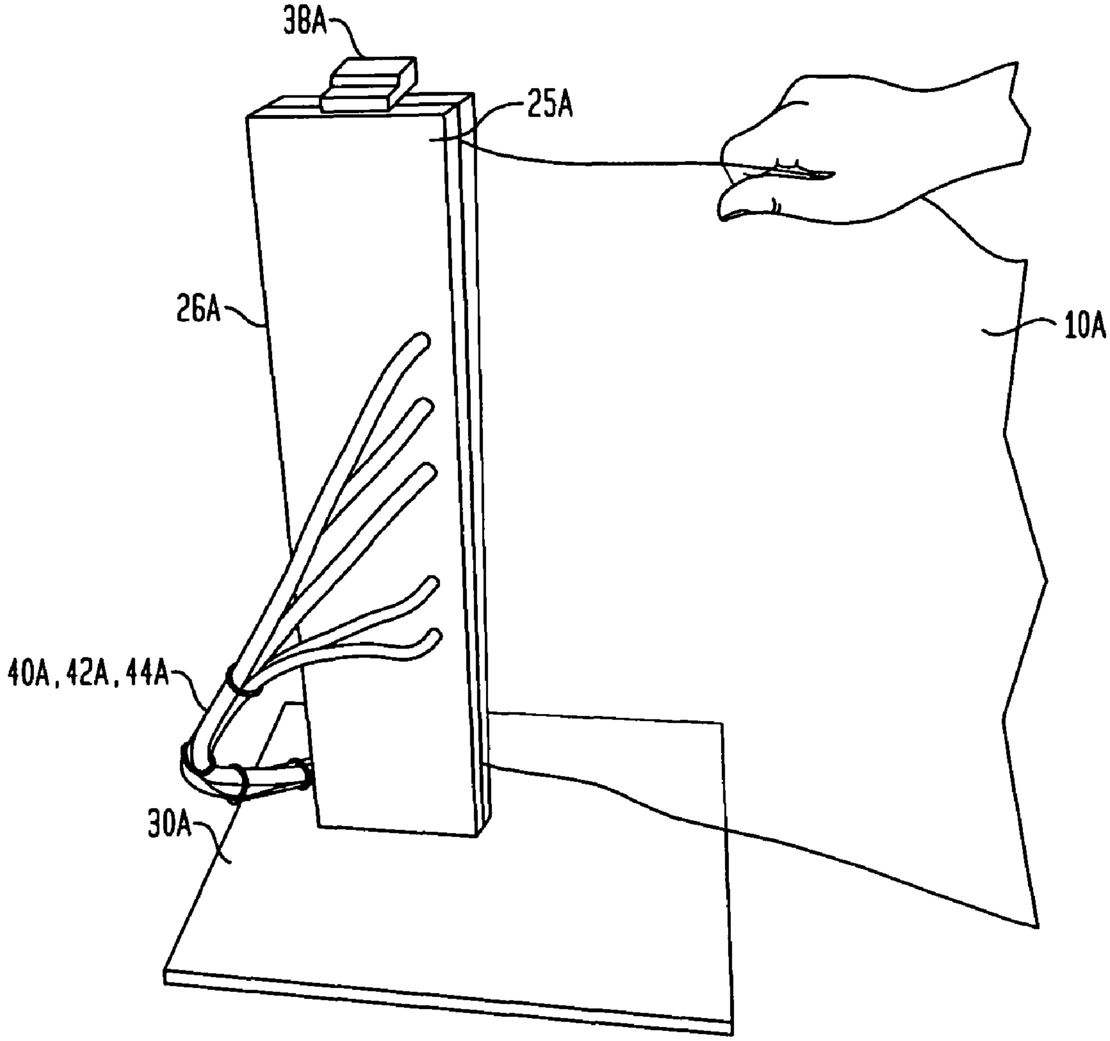
FIG. 11A is a front view of the wound treatment device and the clamping mechanism of FIG. 8A in a closed position.

As shown in FIG. 6A, once the sheets 16A, 18A have been rolled around the slat 32A, the slat 32A is placed into the indent 34A. Thereafter, as shown in FIG. 7A, the second leg 26A is pivoted up toward the first leg 25A. A fastening device such as a clamp 38A, located on the first leg 25A at a remote end from the base 30A, is used to releasably couple the first and second legs 25A, 26A together. The clamp 38A can be any type of fastener that releasably couples the two legs together. Although shown and described located on the first leg, it can be placed on the second leg 26A or at any location on the clamping mechanism 24A.

The open second end 14A between the two sheets 16A, 18A forms the access port 22A when the sheets 16A, 18A are spaced apart from each other. The clinician can arrest treatment and depressurize the device 10A if desired, prior to releasing the clamping mechanism 24A to open the access port 22A by separating the two sheets 16A, 18A at end 14A. This helps to conserve the treatment gas. The clinician can administer pillows, medicament or the like to the limb through the access port 22A. Thereafter, the end of the two sheets 16A, 18A are brought together and wrapped around the slat 32A and held in place with the first and second legs 25A, 26A of the clamping mechanism 24A as previously described.

After the treatment has been completed, clamping mechanism 24A can be removed from the flexible device 10A and reused for the next patient, using a new single use flexible wound treatment device similar to the device 10A described herein.

The access port 22A can be the entire length or less than the length of the device 10A. In other words, the access port 22A can comprise sealing and unsealing of the entire length of the second end 14A of the device 10A or can comprise sealing and unsealing an opening less than the entire length of the second end 14A. In that instance, a portion of the sheets 16A and 18A can be permanently affixed to each other, leaving the remaining portion open for the access port 22A. The size of the slat 32A can then vary according to the size of the opening.

In another embodiment of the present invention, as shown in FIGS. 8A-11A, the clamping mechanism 24A can be coupled to a treatment gas supply and the like. In the embodiment illustrated, the second leg 26A of the clamping mechanism 24A includes various ports that couple to various gas or fluid lines and the like. For example, a pressure monitor line 40A, treatment gas inlet line 42A, treatment gas outlet line 44A and an inlet and outlet for inflating other aspects of the device 10A can be included.

A second indent 46A can be formed on either leg of the clamping mechanism 24A, here shown as being formed on the first leg 25A. This second indent 46A can accommodate a second slat 48A fixedly or releasably attached to one of the sheets 16A, 18A of the device. The second slat 48A, similar to slat 32A, may be fixedly attached to one of the sheets 16A, 18A of the device by heat sealing or the like. In another embodiment, the second slat 48A can be separately provided.

The second slat 48A is complementarily configured with ports that align with the pressure monitor line 40A, treatment gas inlet line 42A, treatment gas outlet line 44A and the like. The second slat 48A can then couple to pre-existing holes or openings in the sheets, or form holes or openings in the sheets when the access port is sealed. Holes can be formed by the second slat 48A by including sharp projections on the second slat adjacent the various ports. These sharp projections can perforate the flexible sheets and form holes when the access part is sealed by the clamping mechanism 24A. Forming the holes in one of the sheets allows the various parts to fluidly communicate with the interior 20A of the device 10A. The second slat 48A therefore, is configured to accommodate the existing fluid lines disposed on the device 10A and couples these fluid lines to the clamping mechanism 24A.

The device 10A can have corresponding openings to accommodate the treatment gas inlet line 42A, outlet line 44A or the like so that the interior 20A of the device 10A is in fluid communication with the treatment gas. In another embodiment, the various parts of the clamping mechanism can include tubular projections to extend into the interior 20A, or the air passageways either through the second slat 48A, or through one of the two sheets in the event no second slat 48A is incorporated.

The device 10A can include an inflatable cuff at the first end 12A of the device 10A. The inflatable cuff is configured to inflate and seal against the limb to form a hermetic seal. In this instance, lines providing gas to inflate the cuff can also be provided for in the second slat 48A. Greater detail is provided hereinafter.

Further, as disclosed in U.S. patent application Ser. No. 11/064,581, filed Feb. 24, 2005, entitled "Hyperbaric Oxygen Device and Delivery Methods," which is hereby incorporated by reference, the device can include two sheets of material sealed together at both ends that are then folded over to form the interior 20A. In this manner, pockets can be formed that allow a fluid such as air or treatment gas to inflate the device. The pockets can be formed by sealing the two sheets 16A, 18A together at various locations, forming inflatable passageways. In this instance, gas can be delivered between the sheets to inflate the device and keep it rigid. Thus, lines providing gas to inflate the device itself can also be provided for in the second slat 48A.

When the clamp 38A releases the second leg 26A from being coupled to the first leg 25A, the gas treatment can stop automatically. Specifically, the clamp 38A can be electrically coupled to a sensor or a switch that is coupled to a controller for the device that operates the functions of the device. Thus, opening the clamp 38A can alert the switch which then results in the controller stopping the flow of treatment gas. Closing the clamp 38A can alert the switch which then results in the controller starting the flow. The clinician need not arrest treatment and then open the clamping mechanism. This facilitates ease of accessing the limb. Further, in the event that the clinician forgets to stop the treatment and opens the clamping mechanism, no treatment gas is wasted to the environment because treatment will be arrested automatically with the opening of the clamping mechanism 24A.

Embodiment B

Referring to FIG. 1B, in an embodiment of the present invention, a wound treatment device 10B is illustrated. The device may be constructed in a manner that improves the treatment of a wound while reducing or eliminating concerns associated with forming the device.

The device can present a challenge associated with the materials and methods used to form the device. For instance, the device can be formed using radio frequency ("RF") welding. However, there can be concerns with using this method. Accordingly, materials and methods of forming the device that reduce or eliminate these concerns is desired, while simultaneously improving the efficacy of the device.

As best seen in FIG. 1B, device 10B includes a device housing 12B that forms an interior region or chamber 14B, which is closed at a first end 16B and open at a second end 18B to receive a limb of a patient.

As best seen in FIG. 2B, housing 12B is formed from two flexible sheets, an outer sheet 12Ba, and an inner sheet 12Bb. The sheets 12Ba, 12Bb are arranged concentrically about one another and are joined together to form an inflatable annular wall therebetween. Gas such as air or even oxygen can be used to pressurize the annular space formed between the two sheets upon sealing the sheets together. Thus, the device housing 12B can be inflated into a semi-rigid, cylindrical, shape. The first end of the housing is sealed, forming a closed first end 16B. In one embodiment of the present invention, the first end 16B may be closed off by sealing together the ends of the walls 12Ba, 12Bb. In another embodiment, the first end 16B may be closed off by attaching another sheet (not shown) to the ends of sheets 12Ba, 12Bb, to enclose the first end. The second end 18B can be tapered having an opening that can include a cuff 22B having a diameter smaller than that associated with the diameter of the housing 12B. However, it should be understood that other shapes may be utilized and that the second end 18B need not be tapered.

The housing 12B includes various openings or ports 19B formed on the sheets 12Ba, 12Bb. Coupled to the ports 19B are one or more tubes 20Bb, which are in fluid communication with the chamber 14B. Tube 20Ba is in selective fluid communication with a treatment gas supply source (not shown) through one or more valves (not shown). The treatment gas and its associated valves are controlled by a controller to be described in greater detail herein, which operates the functions of the device. Reference is made to U.S. patent application Ser. Nos. 12/156,465 and 12/156,466, filed May 30, 2008, entitled "Controller For An Extremity Hyperbaric Device," for suitable controllers, the disclosures of which are incorporated by reference herein. Tube 20Bb is in selective communication with a discharge reservoir, including for example, the atmosphere, through one or more valves (not shown). The discharge valves are similarly controlled by the controller and allow gas to be expelled from chamber 14B, to reduce the pressure in chamber 14B during operation of the device 10B.

As noted above, the open second end 18B of the device 10B is configured with a cuff 22B through which the limb is inserted into the device 10B. In one embodiment, the cuff 22B is formed from a configured section of the housing 12B. In this regard, the housing 12B includes a seam 22Ba that is formed between the two sheets 12Ba, 12Bb, to separate the housing 12B forming the chamber 14B from the housing 12B forming the cuff 22B. As seen in FIG. 3B, the cuff 22B is formed from the sealed space between the two sheets 12Ba, 12Bb as a result of the seam 22Ba.

The cuff 22B can be inflated with air or treatment gas through tube 20Bc (which is in fluid communication with a pressurized source of air or the treatment gas through one or more valves) to form an inflatable cuff seal. Cuff 22B encloses around the patient's limb and thereby provides a seal, such as a hermetic seal, against the patient's limb when the device 10B is in use upon inflation of the cuff. Alternately, as described below, cuff 22B may be formed separately and then attached to the housing 12B.

As seen in FIG. 2B, the housing 12B may include a plurality of inflatable passageways 24B that are formed in the space between sheets 12Ba and 12Bb by circumscribing seams 23Bb. Circumscribing seams 23BB are locations where the first and second sheets 12Ba, 12Bb have been sealed together. Passageways 24B are gaps that are formed between the circumscribing seams 23B and are inflated by air or the treatment gas to stiffen and provide rigidity to the housing 12B. Inflation of the passageways 24B can be independent of supplying treatment gas to the chamber 14B or can be coupled therewith. To allow gas flow between the adjacent passageways 24B, the circumscribing seams 23B may terminate at various locations to form a gap 23B along the circumscribing seam 23Ba. These gaps 23Bb provide fluid communication between the adjacent passageways 24B. In this manner, the pressure of the treatment gas may be varied without the housing collapsing on the patient's wound. For example, the pressure in device 10B may be varied between a first positive pressure (above atmosphere) and a second, but lower, positive pressure, or between a positive pressure and a negative pressure (below atmosphere).

The passageways 24B are in selective fluid communication with a supply of pressurized fluid, such as air or the treatment gas, through a tube 20Bd (and one or more valves) so that passageways 24B can be inflated independently of the flow of treatment gas to housing 12B. The flow of gas into the passageways 24B through the valve or valves is also controlled by the controller that operates all of the functions of the device. Additional detail on the controller is provided below.

Returning to FIG. 1B, a feature that may be incorporated into device 10B is an air pillow 25B. Air pillow 25B can be located in chamber 14B and can be formed from a third sheet of material 12Bd overlying the inwardly facing sheet 12Bb. Sheet 12Bd is sealed at its perimeter to sheet 12Bb to form an inflatable gap for the pillow between sheet 12Bd and 12Bb. The interior of the pillow 25B can be in fluid communication with a supply of air or treatment gas through a tube 20Be and one or more valves so that pillow 25B can be separately inflated similar to passageways 24B and cuff 22B. However, inflation of the pillow can be done along with providing the treatment gas to the device 10B. When inflated, pillow 25B provides support for the patient's limb when the limb is inserted into the chamber 14B. The pillow 25B can be placed at any location within the interior, i.e., adjacent the first end, second end or therebetween, as desired. Although a single pillow is described herein, a plurality of pillows, having varying sizes can be formed in a similar manner and can be placed at various locations inside the housing. For an example of suitable passageways, a pillow, and an inflatable cuff, reference is made herein to U.S. Patent Pub. No. 2006/0185670, entitled "Hyperbaric Oxygen Devices And Delivery Methods," which is hereby incorporated by reference.

As noted above in the illustrated embodiment, the housing 12B is formed from two or more sheets of material. The sheets may be single ply sheets or multi-ply sheets. For example, a suitable material includes a material selected generally from a group of resinous polymer materials that have little or no stretch. More specifically, examples of suitable materials include nylon coated with either ethyl vinyl acetate ("EVA") or polyethylene heat sealable material which is available from the Bemis Company of Neenah, Wis. Alternately, the material can be a polyester coated with either EVA or polyethylene which is available from E.I. du Pont de Nemours of Wilmington, Del.

Nylon material is easier to cut with conventional die-cutting equipment. Further, the dies have a longer lifetime cutting nylon than with other materials. For either material, the coating of EVA or polyethylene provides a heat-sealable surface, which facilitates the easy construction of the hyperbaric wound treatment device. The heat sealable coating can be applied to one side of the non-stretchable fabric or at locations that will be heat-sealed.

The preferred method of heat sealing is described in U.S. Pat. No. 6,881,929, entitled, "Portable Heat Sealer," which is hereby incorporated by reference. This patent discloses the use of segmented heat sealing in order to accommodate a variety of fabric thicknesses in a single heat-sealing cycle. The result is a product which has stronger bonds and can be constructed with significantly less sealing machine cycle time, thus saving manufacturing costs. One advantage of segmented heat sealing compared to RF welding used in the prior art is that fewer manufacturing steps are required to build the product. Further, RF fields are eliminated during manufacture. Moreover, this process has none of the concerns that can be associated with the polyvinyl acetate ("PVA") utilized in certain wound treatment devices.

Referring to FIGS. 2B and 4B, device 10B is formed from two or more sheets 12Ba, 12Bb, with each sheet cut from a sheet of suitable material described above as at step 40B. A die cutting apparatus can be used. Then the sheets 12Ba, 12Bb are folded and sealed to form the housing 12B.

In addition to cutting the outline of the device 10B, the die cutting apparatus may also be used to cut out ports 19B into the sheets 12Ba, 12Bb in order to provide one or more connection points for tubes 20B. These additional openings may be formed either simultaneously with the outline of the respective sheet or after the outlines have been cut. The pillow 25B may also be cut at this time. After being located in the ports 19B, tubes 20B are then heat-sealed to the sheet 12Ba, 12Bb at step 50B. As described below, tubes 20B are typically heat-sealed to sheets 12Ba, 12Bb prior to heat sealing the edges of the sheets together.

After tubes 20B are heat-sealed to the sheet 12Ba (or sheets 12Ba and 12Bb in the case of tubes 20Ba and 20Bb) at ports 19B, the edges of the sheets are heat sealed together to form housing 12B, passageways 24B and cuff 22B. Once sealed together, housing 12B can then be folded so that its top and bottom edges are generally aligned and its side edge is aligned with sheet 12Bc. The top and bottom edges and side edge, which form the housing 12B wall and closed first end 16B are then heat-sealed using the heat sealing techniques referenced above, as at step 55B. As noted above, optional components, such as pillow 25B, may be formed by another sheet or blank that is placed over the sheets and then heat-sealed to the housing at its respective edges to thereby form a space between the additional sheet and the housing 12B.

At step 60B, cuff 22B may be separately formed from the housing 12B, or formed integrally therewith. In this case the cuff is formed separately, it can be prepared from a roll of continuous polyethylene tubing. Polyethylene tubing is manufactured by an extruder which outputs a continuous tube of polyethylene material. Such material is available from a variety of vendors such as Eastern Packaging of Lawrence, Mass.

Further, cuff 22B is optionally manufactured without any slip-agents that could cause the material to become slippery. While it is desirable to incorporate such agents into certain products that are handled by automated machinery, such agents in an application such as this, can cause the cuff to slide off the limb.

During the cuff preparation stage at step 60B, a tube 20B for filling the cuff with a gas is attached, such as by heat sealing, to an appropriate length of the polyethylene tubing material which forms the cuff 22B. The polyethylene tubing material length has no seam when a length of it is chosen for forming the cuff. Thus, at this juncture, the cuff material resembles a hollow cylinder as shown in FIG. 3Ba. Thereafter, the polyethylene tubing material is folded over itself forming a first sheet 22Ba on the outside and a second sheet 22Bb on the inside. In this manner, the folded polyethylene tubing material resembles a double walled hollow cylinder wherein the double walls are connected to one another at a first cuff end 22Bc. At a second cuff end 22Bd, the two sheets 22Ba, 22Bb are not connected.

This folded tubing length forming the cuff 22B is placed inside the housing 12B near its second end 18B. The second cuff end 22Bd is placed adjacent the second end 18B of the housing 12B as shown in FIG. 3*c*. These sheets are then heat sealed simultaneously, forming a circumferential seam between the housing 12B, and the cuff sheets 22Ba, 22Bb. Thus, there is no seam along an axis of the cuff 22B.

Once the cuff 22B is attached, the polyethylene tubing material can be pulled inside out to form a limb cuff external to the device. The cuff sheets 22Ba, 22Bb can also be attached to the housing 12B in such a way as to have the cuff located partially within the housing 12B. The cuff can also be disposed either entirely within the device housing 12B or entirely without.

To reduce the number of manufacturing steps, the attachment of cuff 22B to housing 12B by heat sealing may be accomplished at the same time sheets 12Ba and 12Bb are heat-sealed to form the housing 12B as at step 70B. Similarly, passageways 24B and/or the pillow 25B may be formed at the same time sheets 12Ba and 12Bb are heat-sealed to form the housing 12B, so that passageways 24B, and/or pillow 25B, and cuff 22B may all be heat-sealed at the same time as the sheets forming housing 12B and forming pillow 25B are placed in the heat-sealing machine.

After these components have been positioned in the heat sealing machine but before heat is applied, at step 80B, a 1/32" thick Teflon™ sheet available from McMaster Carr of Robbinsville, N.J., is placed within cuff 22B where the cuff will be heat-sealed to the housing 12B of the device 10B. The Teflon™ sheet prevents cuff 22B from being heat-sealed to itself during the heat sealing process. The other components, such as the housing 12B, passageways 24B and pillow 25B, of the device will not self-seal because the heat-sealable coating can be placed on only one side of the material or at locations where heat sealing is desired.

Optionally, at step 90B, the entire device 10B may be heat-sealed together in a single step utilizing the method described in U.S. Pat. No. 6,881,929, entitled, "Portable Heat Sealer," which is hereby incorporated by reference. This patent teaches setting the various segments or areas of the sealing die to different temperatures in order to seal the device in a single step. For example, additional heat is applied for areas with greater thickness, such as where three layers of material are welded, for example, at cuff 22B, than with thinner areas, where fewer layers may be heat-sealed.

After the device 10B has been heat-sealed into a single unit, it is optionally pressure tested at step 100B to ensure that there are no leaks. For example, all of the components of the device 10B may be tested for their ability to hold pressure, without stretching.

Referring to FIG. 5B, a pressure waveform from one embodiment of the operation of a hyperbaric wound treatment device of the present invention has a linear form. Because the fabric of the hyperbaric wound treatment device may have little or no stretch, the pressure waveform of the treatment gas ramps up to the hyperbaric pressure maximum 30B at a linear rate and then rapidly drops off as the gas is purged from the chamber 14B, so that the device 10B may provide a more rapid pulsed wound treatment. This pulsing may result in improved therapeutic benefit for the patient.

In another embodiment of the present invention, as best seen in FIG. 6B, a flexible hyperbaric wound treatment device 110B includes a housing 112B, which is formed from a single sheet of material, and a chamber 114B. The sheet is folded and heat-sealed at an outer seal 120B, similar to the previous embodiment. For examples of suitable material for the sheet, reference is made to the first embodiment.

Housing 112B includes an inflatable cuff 190B and one or more regions or sections each with a plurality of passageways 140Ba. In an embodiment of the present invention, the cuff 190B may be wholly external, in that the cuff is formed external to the chamber 114B. In another embodiment of the present invention, the cuff 190B may be formed either entirely or partially within the housing 114B as described in U.S. patent application Ser. Nos. 12/156,465 and 12/156,466, previously mentioned.

Each group of passageways 140B can be formed by a second sheet 141B that is heat sealed at its perimeter by a seam 142B to an interior or exterior portion of housing 112B. The space between the second sheet forms a gap, which is divided by a plurality of spaced seams 144B that extend across the sheet but terminate before the perimeter seal 142B to allow air flow between the adjacent passageways. Similar to passageways 24B, passageways 140Ba stiffen at least a portion of housing 112B upon inflation.

Further, the device 110B includes ports 160B and 170B (similar to the first embodiment) to enable the treatment gas to enter and exit the device 110B. A third port 180B for each group of air passageways 140B is provided and couples to another tube to inflate the air passages 140B with air or the treatment gas.

The sheet or blank forming housing 112B is cut to form a curved or tapered transition 145B that extends from an area adjacent the cuff 190B to a portion of the device 110B spaced from the cuff 190B, for example adjacent the second passageway 140B. This curved transition 145B reduces mechanical stress on the device during inflation. The use of the EVA coated nylon for fabricating the device 110B, and particularly the curved transition 145B, is advantageous because the coated nylon exhibits very little stretch, while providing rigidity.

Similar to cuff 22B, cuff 190B can be formed out of a continuous tube of polyethylene which is heat-sealed to the device 110B with a seal 230B. The cuff 190B is positioned inside housing 114B between a patient's limb and the inside wall of device 110B and is inflated using a cuff port 200B coupled to a valve (not shown). The cuff 190B is inflated and seals against the limb. Then as the housing 114B is inflated through port 160B, the pressure from the gas within the housing 110B exerts pressure on cuff 190B to further seal cuff 190B hermetically to the limb.

When the pressure inside the flexible device 110B reaches its peak, the circumferential heat seal 230B, which joins cuff 190B to flexible device 100B, can experience some strain. Due to the manner of packaging and transporting the device 100B, a first crease 210B and a second crease 220B can form at either end of the cuff 190B as the device is laid flat. Therefore the first and second creases 210B, 220B are reinforced to provide strain relief to ensure that the flexible device 100B does not tear during the period of maximum pressurization. It is preferred that the reinforced areas consist of additional material welded over the seam as shown in FIG. 6 although other types of reinforcements can be utilized.

Embodiment C

In an embodiment of the present invention, a triple modality wound treatment device is configured to provide one or more therapies, including compression therapy, evacuation therapy, and/or hyperbaric gas treatment therapy to treat a wound. The combination of all three modalities is believed to provide additional benefits not previously seen with any one therapy. When intermittent compression is combined with negative pressure, interstitial fluid is removed, allowing for reduced swelling. Reduced swelling in turn, increases blood flow to the area, which, when combined with oxygen, provides improved granulation in the tissue to provide enhanced treatment over prior art wound treatment methods.

In one embodiment of the present invention, the device includes at least two individual compartments. Each compartment can be a wound treatment separated by an inflatable divider cuff that seals against the patient's limb. The individual cuffs can each contain a separate valve so that each cuff may be separately inflated with a gas, such as air. Thus, if a cuff, upon inflation, would contact a wound, that cuff need not be inflated. Therefore, a number of inflatable cuffs are provided, and a clinician can select which cuffs to inflate.

The single use treatment device of this embodiment can have a highly absorbent foam liner at the bottom of the device, allowing the absorbent liner to capture the discharged fluids. The device can be hermetically sealed around the extremity above the wound site. The wound can be elevated inside the device by a support structure, such as a pillow, that prevents the wound from coming in direct contact with the absorbent liner.

In an embodiment of the present invention, a wound treatment device 10C is illustrated in FIG. 1C. The device 10C includes a housing 8C having an open end 12C and a closed end 14C. Adjacent the open end 12C is a seal 16C that encircles a limb and forms a hermetic seal against the limb to prevent the treatment gas from escaping through the seal 16C. The seal 16C may be any type of seal, such as a tape seal, or a latex seal. Further, the seal may be similar to that disclosed in U.S. patent application Ser. Nos. 12/156,465 and 12/156,466 both previously mentioned. The device 10C includes an interior chamber 18C that accepts the treatment gas to treat the wound. The device 10C can also include an absorbent liner 20C that may be adjacent a bottom of the interior 18C to capture debris or fluids. Further, the device 10C can include a pillow 22C or support for the limb so that the patient is comfortable.

FIG. 2C is a perspective view of a cross-section of the device 10C in an embodiment of the present invention. The device 10C incorporates a plurality of divider cuffs 24C that are placed at various locations in the interior 18C of the device 10C. The divider cuffs 24C include a center 26C, and can be in a ring-like or donut configuration, with the center 26C accommodating and encircling the limb upon inflation.

Each of these divider cuffs 24C are connected to an individual valve 30C that allows each of the divider cuffs 24C to be individually inflated. These valves can be coupled via a hose 31C to a gas source I. This gas source I can be any type of gas, preferably air. Another valve (not shown) can be used to vent the gas to the surroundings in order to deflate the cuff 24C. In the event that one of the cuffs would contact the wound upon inflation, that particular cuff 24C may be left deflated.

FIG. 3Ca is a cross-sectional diagram of one of the divider cuffs 24C and FIG. 3Cb is a perspective view of one of the divider cuffs 24C. Specifically, in one embodiment, the cuff 24C includes a first wall 23C that runs orthogonal to the axis of the opening 26C. Further, the cuff includes a second wall 25 that runs parallel to the first wall 23C. Next the cuff includes an inner wall 27C that connects the first and second walls, 23C, 25C respectively. Lastly, the cuff 24C can include an outer wall 29C that is fixedly attached to the interior of the device housing 8C. Optionally, the cuff outer wall 29C can be the interior of the device housing 8C. A gap is created between these walls and is inflatable; gas entering through the valve 30C enters this gap and inflates the cuff 24C.

Preferably, the first and second walls 23C, 25C are formed of a material having a thickness greater than that of the inner wall 29C. This configuration allows for the thinner inner wall 29C to expand and stretch to a degree greater than the stretch at the thicker first and second walls 23C, 25C when the cuff 24C is inflated. Such stretching at the inner wall 29C allows for the opening 26C in the cuff 24C to seal against the limb being treated, forming a hermetic seal.

In the instance that one of the cuffs would contact the wound, that particular cuff can be left uninflated. Then the opening 26C would be slack and not contact the limb. When the divider cuffs 24C are inflated, the divider cuffs 24C expand to seal around the limb and form a plurality of isolated compartments. Although five compartments (I, II, III, IV, and V) are shown in FIG. 2C, any number of divider cuffs 24C may be incorporated into the interior to create any number of compartments. Thus, individual compartments are formed between each of the divider cuffs 24C and between either end of the interior 18C.

To provide compression therapy, device 10C includes at least two compartments. Optionally, there are between two and thirteen compartments. However, there may be as many compartments as desired. The compartment I adjacent the closed end 14C is defined as the distal compartment, while the compartment V adjacent the open end is considered the proximal compartment.

The pressure in each of the compartments can be individually controlled and adjusted. Each compartment has an inlet valve 15C and an outlet valve 17C. The valve 15C is coupled via a hose to a gas source II. This gas source II is preferably a treatment gas, such as oxygen. However, the cuff valve 30C may also be coupled to gas source II, eliminating the need for gas source I. Thus, a second source of gas is optional.

Thus, the inlet valves 15C of all the compartments are coupled to gas source II. The outlet valves 17C for each of the compartments are coupled, via a hose, to vent the treatment gas to the surroundings upon completion of the treatment.

Once a limb has been placed within the interior 18C of device 10C and the seal 16C has been closed around the limb, treatment can begin using any of the three modalities described herein. The three modalities may be combined in various ways and in varying sequences. For example, treatment may be provided that utilizes just hyperbaric gas therapy and compression therapy without evacuation therapy. Alternatively, just evacuation therapy alone may be provided. Thus, various combinations can be utilized.

For instance, a limb may be inserted into the housing 8C. The seal 16C is utilized to seal the housing 8C against the limb. Thereafter, the selected divider cuffs 24C are also inflated against the limb to seal off each of the various compartments from each other. Next, gas therapy may first be provided by filling the interior 18C with a treatment gas such as oxygen, by utilizing inlet valve 15C. Thereafter, the treatment gas within each individual compartment I-V may be compressed by increasing the amount of the gas and therefore pressure of the treatment gas in each compartment. Sequentially increasing pressure in each compartment, thereby applying compression, from the distal portion of a limb to the proximal portion of a limb may be advantageous. Therefore, compression can occur in a sequential manner from the distal compartment to the proximal compartment, by increasing the amount of the treatment gas and therefore pressure.

Accordingly, compartment I may initially be compressed. Then, the treatment gas within compartment II may be compressed, and so on. Once all the compartments have been compressed for a time, all of the compartments are returned to ambient pressure by removing some or all of the treatment gas from each compartment. Treatment gas may be removed through the outlet valves 17C. Thus, treatment gas may just be vented to the surroundings upon completion of the treatment. Further, it is also possible to vent one of the compartments without venting all of the compartments. Correspondingly, it is also possible to add treatment gas or provide negative pressure to one of the compartments without doing so to the other compartments.

The device 10C can be coupled to a controller that operates the functions of the device, including the valves, the cuffs, and the gas source. The controller may be any type of computer, microprocessor, or the like as known in the art. Additional detail is provided hereinafter.

FIG. 4C is an illustration of a method according to an embodiment of the present invention. At step 100C, a limb is placed inside the device 10C; and at step 102C, the device is sealed with the seal 16C, inflated against the limb. Thereafter, at step 104C, air trapped within the interior 18C is evacuated via the outlet valves 17C. Then, at step 106C, treatment can begin with evacuation therapy, taking advantage of the initial evacuation of the existing air in the interior 18C. Then gas treatment and compression therapy can follow. Having the compression therapy follow the gas treatment therapy takes advantage of the treatment gas present in the device 10C during gas treatment.

FIG. 5C illustrates one embodiment of the types of therapy cycles that may be performed. At the outset, a limb may be inserted into the housing 8C. The seal 16C is then utilized to seal the housing 8C against the limb. Thereafter, the selected divider cuffs 24C are also inflated against the limb to seal off each of the various compartments from each other. Next, at step 200C, upon evacuation of the existing air within the compartments, a treatment gas is introduced into the interior 18C. Optionally, the treatment gas is oxygen, but any other suitable gas may also be employed. Thereafter, at step 202C, sequential compression of the treatment gas from the distal compartment I to the proximal compartment V is employed. Next, at step 204C, all of the compartments are evacuated of the treatment gas and evacuation therapy is performed for a period of time. Finally, at step 206C, this particular treatment is repeated as desired. Although FIG. 5C provides one embodiment of the present invention, a combination of the three modalities may be utilized in any sequence as desired, or even just one modality may be utilized. Various timeframes and time periods may also be employed.

In an embodiment of the present invention, the treatment can occur in cycles such as, for example, a 90-minute cycle. A timer coupled to the device may be incorporated to determine the time periods for the cycles. The first session can be the evacuation cycle, which can last for approximately ten minutes, followed by an approximately 20-minute cycle of treatment gas therapy and then intermittent compression therapy using the treatment gas as a compression medium. This 30 C minute cycle can then be repeated twice more during the session, allowing for a total 90-minute cycle. Although these particular time ranges have been described, the variety of time ranges and number of cycles and repetitions may be varied as desired. The device offers the ability to utilize the treatment gas, such as oxygen, on a continuing basis.

Evacuation therapy assists in granulation and applies controlled localized negative pressure to help slowly and uniformly draw the wounds closed. Evacuation therapy also helps remove interstitial fluids, allowing tissue decompression while helping to remove infectious materials from the wound. Further, evacuation therapy provides a closed moist environment and promotes flap and graft survival. The device 10C applies non-contact evacuation therapy to a wound site. With each individual compartment pressure being adjusted, therapy may then be applied directly to the area.

The pressure range can be between 25 mm Hg to 200 mm Hg above ATA or ambient pressure. By applying controlled negative pressure, the device 10C aids in the removal of fluids backing up interstitial tissue due to a breakdown of the lymphatic drainage system commonly known as lymphedema. The fluids drained from the wound are absorbed into the absorbent liner 20C placed within the device 10C, which is configured to absorb the fluids discharged from the wound, but which is spaced from the wound as will be more fully described below.

As noted above, device 10C may be used to apply gradient sequential compression therapy. Sequential compression therapy reduces swelling and fibrosis, or hardening, which is a chronic inflammatory condition stemming from the accumulation of fluid in the extremity. Further, sequential compression therapy improves circulation and wound healing, and is an effective prophylaxis for venous thrombosis.

Sequential compression therapy is designed to release edema from an extremity that progressively releases fluids in a distal to a proximal direction. First, pressure is established at the distal end of a limb, such as the fingers or toes in either an arm or a leg, respectively, and progresses in a proximal direction toward the proximal end of the limb until the entire limb is compressed. For example, the pressure may range between 5 to 100 mm Hg in the compression phase for 30 seconds, followed by a 5 second or less compression phase whereby the pressure is decreased for a time. These time ranges may vary and are recited as examples only.

FIG. 6C is an illustration of another embodiment of the present invention showing a leg placed on the absorbent liner 20C. Optionally, the absorbent liner can be approximately four inches thick and can be placed at the base of the device 10C along the entire length. The absorbent liner 20C can include a removable portion 32C that has a depth less than the height of the liner, such as two to three inches in the case of a four inch liner. Thus, if a portion of the leg, such as the heel, has the wound and the wound is sensitive to contact with the absorbent liner 20C, the removable portion 32C can be detached such that the heel would not contact the absorbent liner 20C. The dimensions provided herein can be varied as desired.

Additionally, a portion of the liner 20C, for example, a one inch layer, can remain at the bottom of the liner 20C for debris absorption. The remaining portion absorbs the fluids discharged from the wound during evacuation of the fluid during treatment, even though the removable portion 32C of the liner 20C has been detached to accommodate the wound.

In another embodiment of the present invention, a number of individual absorbent liners 20C may be placed inside the compartments. These ranges of sizes, depths, and shapes of the removable portion 32C are exemplary only, and any variety of shapes and sizes may be utilized. The removable portion 32C can be easily torn out by a user without requiring any tools. Generally, the removable portion 32C can be formed by perforating the liner 20C, or it may be formed in any other suitable manner.

Embodiment D

Referring to FIG. 1D, a wound treatment system is schematically illustrated, according to one embodiment of the present invention. The system includes a wound treatment device 10D and a control system 16D for operating various functions of the device 10D as previously described In particular, the device 10D incorporates a pressure compensating seal, which reduces leakage and allows the limb seal to be adjusted automatically without intervention from either the patient or a clinician.

The device 10D includes a hyperbaric chamber or housing 12D with a cuff 45D at least at one end that can seal a limb in the housing 12D. The housing 12D can be selectively filled with a treatment gas or air supplied by a treatment gas source. The control system 16D controls the flow of treatment gas into housing 12D and the seal achieved by the cuff 45D. The device 10D is similar to that disclosed in U.S. patent application Ser. Nos. 12/156,465 and 12/156,466 a previously stated.

The control system 16D operates the functions of both the housing 12D and the cuff 45D. The control system 16D includes a microprocessor 60D, a plurality of valves, and a plurality of pressure sensors. The pressure sensors monitor pressures inside the housing 12D and the cuff 45D and communicate those pressure readings to the microprocessor 60D. Valves associated with the housing 12D and the cuff 45D allow for treatment gas, air or other fluids to inflate or deflate the housing or the cuff as determined by the microprocessor 60D. In this manner, the control system 16D can monitor the pressures in the cuff 45D and the housing 12D to adjust the respective pressures accordingly by opening and closing certain valves and by delivering and exhausting fluid into or out of the housing 12D and the cuff 45D.

Specifically, treatment gas from a treatment gas source or pump (not shown) is directed into the housing 12D through inlet port 75Db and through a housing supply valve 65D. As treatment commences, treatment gas is supplied to the limb in such a manner. Correspondingly, when treatment ends, the treatment gas can be removed or exhausted from the housing 12D through a housing exhaust valve 50D and exhaust port 75Da. Further, the supply and exhaust valves 65D, 50D, respectively, are controlled by the microprocessor 60D based on the pressures within the housing 12D.

A housing pressure sensor 70D, in communication with the interior of the housing 12D, is monitored by the microprocessor 60D through a control port C. Any type of pressure sensor can be used, such as a pressure transducer or the like. Thus, the pressure of the treatment gas within the housing can be continuously monitored and controlled by the microprocessor 60D in real time. If the pressures are too high, the exhaust valve 50D can be opened and treatment gas can be removed from the housing 12D to lower the pressure. If the pressure is too low, additional treatment gas can be provided to the housing 12D through the supply valve 65D.

The seal provided by the cuff 45D about the patient's limb can be operated and monitored in a similar manner. The cuff 45D is inflatable and can be formed in a manner described more fully below. A gas, such as treatment gas, ambient air or the like can be used to inflate the cuff 45D. Thus, the cuff 45D can be in fluid communication with the same treatment gas source that provides gas to the housing 12D or can be in fluid communication with a second gas source (also not shown).

Specifically, the cuff 45D is in fluid communication with a cuff gas source through a cuff supply valve 80D and gas from the cuff gas source through inlet port 75Db which supplies the treatment gas. In another embodiment, an inlet port (not shown) for the supply of cuff gas from another source can be provided. The pressure in the cuff 45D is measured by a cuff pressure sensor 85D, such as a pressure transducer or the like, which is monitored by microprocessor 60D through control port E. Further, the cuff 45D includes a cuff exhaust valve 55D, which removes gas from the cuff 45D through cuff exhaust port 75Dc.

As discussed with respect to the housing 12D, the microprocessor 60D monitors and adjusts the pressure within the cuff 45D, during operation of the device 10D when treating a patient. The microprocessor 60D uses pressure readings within the cuff 45D, obtained from the cuff pressure sensor 85D, to add gas to the cuff 45D through the cuff gas supply valve 80D when the pressure inside the cuff is low. Correspondingly, the microprocessor 60D removes gas from the cuff 45D through the cuff exhaust valve 55D when the pressure inside the cuff is too high.

Most often pressure loss within the housing occurs as a result of an inadequate seal being formed between the cuff 45D and the patient's limb. With prior art wound treatment devices, seals between the device and the limb were usually taped. So when there is a leak, the patient or more often a clinician, has to stop the treatment and re-tape the device to the limb. This is tedious, wastes precious time in wound healing and often requires the assistance of a second person. As such, leaks can usually be stopped by forming a more effective seal with the limb. In an embodiment of the present invention, a hermetic seal to prevent pressure loss can be accomplished without the need for a clinician or the patient to re-tape the seal with the limb, as is necessary with prior art wound treatment devices.

Thus, with an embodiment of the present invention, it will not be necessary to stop treatment and have a clinician re-tape a seal against the limb. The patient, through the control system 16D can be ensured of an effective seal throughout the course of treatment. Generally, when a leak is detected in the housing 12D, by way of a decreasing pressure from the housing pressure sensor 70D, the cuff pressure is increased by the addition of gas to the cuff 45D so that a tighter seal is formed between the cuff and the limb. Correspondingly, additional treatment gas can be supplied to increase the pressure in the housing 12D. Subsequent pressure readings can be taken to determine whether the leak has been reduced or eliminated and the cuff pressure can be adjusted accordingly, i.e. lowered if the leak has been reduced or eliminated. If the leak continues, additional pressure may be provided to the cuff to further reduce the leak. In this manner, the wound treatment system of the present invention provides a pressure compensating seal.

The microprocessor 60D can be configured with various methods in order to provide the pressure compensating seal with positive feedback. Two example methods are disclosed herein.

In one form of the present invention, treatment gas flows into housing 12D through valve 65D, with the pressure in the housing 12D detected by the housing pressure sensor 70D and monitored by the microprocessor 60D. Treatment gas is supplied to the housing 12D through the housing supply valve 65D with a pressure waveform shown at line 88D in FIG. 2D. Similarly, air or treatment gas flows into cuff 45D through valve 80D, with an initial cuff pressure as set by microprocessor 60D, which is shown at line 90D in FIG. 2D. Microprocessor 60D monitors pressure at cuff 45D by reading the pressure sensor signals generated by sensor 85D.

The microprocessor 60D then monitors the pressure in housing 12D, which is increased gradually using the housing supply valve 65D. If the pressure plateaus as shown, for example, at line 95D, which is below desired hyperbaric therapy pressure levels, a leak may be present. In this example, the maximum pressure is about 50 mm Hg or 810 ATA. Therefore, if the pressure falls below about 50 mm Hg, a leak is present. As such, the microprocessor 60D increases the pressure of cuff 45D to a higher level indicated by line 100D and the cycle is repeated.

In the second cycle, if the microprocessor determines that the pressure has again reached a plateau at line 110D, the microprocessor 60D again increases the pressure level in cuff 45D which is shown as line 115D. This type of cycle can be repeated. When the correct level of the hyperbaric pressure 120D is attained in the housing 12D without plateauing, this indicates an adequate seal has been achieved for that pressure and hyperbaric therapy can then be performed. If during the course of therapy, the correct pressure level for the hyperbaric therapy is not maintained, the microprocessor 60D readjusts the pressure in cuff 45D to reestablish a hermetic seal.

In another embodiment of the present invention, as illustrated in FIG. 3D, the microprocessor 60D can test the seal obtained by the cuff 45D to ensure that an adequate seal has been provided. The microprocessor performs this test by turning off the flow of the treatment gas into the housing 12D at a particular point during a treatment cycle and measures the rate of the decrease of pressure in the housing 12D. For example, once the pressure in housing 12D has reached a level indicated by the point 125D, the housing supply valve 65D is closed to stop the flow of the treatment gas into the housing 12D.

Where the cuff pressure is adequate to create a hermetic seal with the limb 30D, the pressure in the housing 12D remains steady as shown by the flat line 130D. Thus, there is no leak at the cuff 45D. Having determined this ideal situation, the microprocessor 60D then continues with the treatment and adds treatment gas to the housing 12D using the housing supply valve 65D. This increase in housing pressure 12D is shown as line 135D. Eventually the pressure in housing 12D reaches the maximum pressure of 50 mm Hg. which is shown as 140D on FIG. 3D. At this point the microprocessor 60D can open the housing exhaust valve 50D and remove some treatment gas from the housing 12D depending upon the treatment process, thereby lowering the pressure within the housing 12D.

Where the cuff pressure is not adequate to create a hermetic seal with the limb, the pressure in the housing 12D drops, as indicated the line 130D', indicating a leak at the cuff. As a result of a leak being detected, the microprocessor 60D can increase the cuff pressure to a higher level in order to provide a better seal. This cycle of stopping the flow of treatment gas into the housing 12D and measuring the pressure within the housing can be repeated until a steady state line, similar to that indicated by line 130D is achieved, indicating that a leak has been eliminated. Thereafter, the microprocessor can continue treatment by adding treatment gas into the housing 12D as indicated by 135D' until the maximum pressure is reached at 140D'.

At this point, once again, the housing supply valve 65D can be closed and the housing exhaust valve 50D can be opened to remove the treatment gas from the housing and return the housing to ambient pressure as prescribed by the treatment process.

The relationship between the housing pressure and cuff pressure is shown in FIG. 4D. As treatment begins inside the housing 12D, an increase in the housing pressure is indicated at line 160D, having a positive slope. A steady state pressure in the cuff 45D is represented at flat line 155D. At some time, t=1 a leak occurs wherein the pressure inside the housing drops and is illustrated with the line 165D having a negative slope. To compensate for this pressure drop the microprocessor 60D increases the pressure in the cuff 45D as indicated by line 170D. The resulting increase in pressure in the housing, as shown by line 167D, having a positive slope, indicates that the leak has been reduced.

Between t=2 and t=3, a pulsed treatment cycle ensues whereby the pressure in the housing is decreased to zero, indicated by line 168D and then increased, as indicated by line 169D. As the pressures within the housing correspond to the supply and exhaust of treatment gas, according to predetermined measurements, no leak is indicated and the pressure within the cuff remains steady, as shown by line 170D.

After t=3, nearing the end of the treatment, the pressure inside the housing increases even though no additional treatment gas has been supplied, as indicated by line 176D having a positive slope. As a result, the microprocessor 60D decreases the pressure in the cuff to a level indicated by line 180D and allows for some treatment gas to escape. At the end of the treatment, the microprocessor 60D stops the flow of treatment gas into the housing, returning the pressure within the housing to zero, as indicated by line 177D having a negative slope.

Reduction of pressure in the cuff 45D may be done if the patient is uncomfortable or if the pressure in the cuff 45D is so great as to cause constriction of the blood flow in the limb, i.e.

a tourniquet effect. Thus, the microprocessor 60D adjusts the pressure in the cuff 45D to prevent leakage of the treatment gas from the housing 12D while reducing or eliminating a tourniquet effect.

A flow chart of this cycle is shown in FIG. 5D. Here, in an embodiment of the present invention, the pressure in cuff 45D is set to a nominal value, at step 190D. The hyperbaric treatment is then initiated at step 200D. As the housing reaches its first pressurization at step 210D, the flow of treatment gas into the device 10D by housing supply valve 65D is terminated and the rate of leakage is measured using the housing pressure sensor 70D as shown at step 220D. Based on the leakage curve measured by microprocessor 60D, appropriate adjustments are made to the cuff pressure at step 230D, and the treatment cycle resumes at step 240D.

The method described herein can also be applied to devices which require a steady state pressure for wound treatment as opposed to the cyclical pressure which is used for pulsed hyperbaric treatment. Examples of such steady state devices include those used to treat lymphedema, iron lungs, and conventional glove boxes. An example of the relationship between the housing pressure and the cuff pressure under a steady state treatment is illustrated at FIG. 6D.

In this example an initial level of pressure is obtained at the cuff 45D, shown at the line 245D in FIG. 6D. The treatment gas supplied to the housing 12D is turned on for a period of time as indicated by line 250D. At t=1, a test is performed where the treatment gas is momentarily turned off as indicated at point 255D. The ensuing drop in pressure, as indicated by line 260D, having a negative slope, shows that there is a leak at the cuff. Accordingly, the cuff pressure is increased at t=2 to a higher level, as indicated by line 265D.

The corresponding increase in pressure within the housing, as indicated by line 270D, having a positive slope, shows that the leak at the cuff has been greatly reduced or eliminated. Thereafter, the pressure in the housing stabilizes and remains steady, as indicated by the flat line 271D. An increase in the housing pressure is indicated at line 275D, having a positive slope. Therefore, the cuff pressure is decreased, as shown by line 277D, allowing the treatment gas to return to a steady state level as shown by line 278D. Various configurations are possible. These example relationships are illustrated to show the relationship between the pressure within the housing and the cuff and how adjustments can be made for leaks and the like. These steps may be repeated and adjusted according to the method of treatment required for effective wound healing.

The device 10D, in an embodiment of the present invention can easily be incorporated to work with a rigid wound treatment device or a flexible wound treatment device. The cuff seal 45D can be adapted and be used in connection with a rigid device as disclosed in "Hyperbaric Wound Treatment Device", filed Nov. 6, 2008, claiming priority to U.S. Provisional Application No. 61/002,085, having Ser. No. 12/291,328 by the assignee of the current application, incorporated by reference herein.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as defined by the appended claims.

What is claimed is:

1. A wound treatment device, comprising:

a flexible housing having an interior for accommodating treatment gas, the housing having:

a first end for accommodating a patient's limb; and a second end remote from the first end having an access port; and a clamping mechanism for sealing and unsealing the access port, the clamping mechanism comprises a first leg, a second leg coupled to the first leg, wherein the second leg is configured to pivotably move with respect to the first leg, a base on which are mounted the first and second legs, and a fastener for fastening the first and second legs together.

2. The device of claim 1, wherein the second end includes an elongated member about which the second end of the housing is coupled.

3. The device of claim 2, wherein the elongated member is enclosed in the clamping mechanism in a sealed state of the access port.

4. A wound treatment device for use with a clamping mechanism, comprising:

a flexible enclosure having a first end configured for sealing against a limb and a second end adapted to form an access port;

wherein the second end is coupled to an elongated member adapted for releasably coupling to a clamping mechanism for sealing and unsealing the access port, wherein the clamping mechanism comprises a first leg, a second leg coupled to the first leg, wherein the second leg is configured to pivotably move with respect to the first leg, a base on which are mounted the first and second legs, and a fastener for fastening the first and second legs together.

5. The device of claim 4, wherein at least one of the first and the second legs includes an indent for accommodating the elongated member.

6. The device of claim 4, wherein at least one of the first or second legs includes ports for fluid lines to provide treatment gas to the flexible enclosure.

7. The device of claim 4, wherein the fastener is coupled to a switch that stops or starts a flow of treatment gas to the flexible enclosure.

8. A wound treatment device, comprising:

a flexible enclosure, having an interior, comprising:

a first end configured for sealing against a limb;

a second end forming a sealable and unsealable access port; and an elongated member about which the second end of the enclosure is coupled thereto, the second end of the elongated member adapted to be releasably coupled to a clamping mechanism comprising:

a first leg;

a second leg movable relative to the first leg;

an indent disposed on an inside surface of at least one of the first and the second legs to accommodate the elongated member and second end of the enclosure coupled thereto; and a fastener for releasably coupling the first leg to the second leg with the elongated member therebetween.

9. The device of claim 8, further comprising a hinge for pivotably moving the first leg about the second leg.

10. The device of claim 8, further comprising a base on which the first and second legs are mounted.

11. The device of claim 8, wherein the flexible enclosure includes a first sheet and a second sheet.

12. The device of claim 11, wherein the first sheet includes the elongated member at the second end.

13. The device of claim 11, wherein the elongated member is fixedly attached to the first sheet.

14. The device of claim 11, wherein the first and second sheets are wrapped around the elongated member.

15. The device of claim 8, wherein the first leg has a first leg indent for accommodating the elongated member.

16. The device of claim 8, wherein the second leg has a second leg indent for accommodating the elongated member.

17. The device of claim 8, wherein at least one of the first or second legs includes ports for fluid lines to provide treatment gas to the flexible enclosure.

* * * * *